(12) United States Patent
Heaton et al.

(10) Patent No.: US 7,700,644 B2
(45) Date of Patent: Apr. 20, 2010

(54) ISOFLAVONOID DIMERS

(75) Inventors: Andrew Heaton, New South Wales (AU); Naresh Kumar, New South Wales (AU)

(73) Assignee: Novogen Research Pty Ltd, North Ryde, New South Wales (AU)

( * ) Notice: Subject to any disclaimer, the term of this patent is extended or adjusted under 35 U.S.C. 154(b) by 0 days.

(21) Appl. No.: 11/909,538

(22) PCT Filed: Mar. 24, 2006

(86) PCT No.: PCT/AU2006/000395
§ 371 (c)(1), (2), (4) Date: Jun. 6, 2008

(87) PCT Pub. No.: WO2006/099681
PCT Pub. Date: Sep. 28, 2006

(65) Prior Publication Data
US 2008/0306140 A1 Dec. 11, 2008

Related U.S. Application Data

(60) Provisional application No. 60/668,609, filed on Apr. 6, 2005.

(30) Foreign Application Priority Data
Mar. 24, 2005 (AU) ............................... 2005901475
Oct. 28, 2005 (AU) ............................... 2005905985

(51) Int. Cl.
*A61K 31/352* (2006.01)
*C07D 493/04* (2006.01)
(52) U.S. Cl. ..................... 514/453; 549/382
(58) Field of Classification Search .................. 549/382; 514/468, 453
See application file for complete search history.

(56) References Cited

FOREIGN PATENT DOCUMENTS

| JP | 09-067362 A | 3/1997 |
|----|-------------|--------|
| WO | 02/070502 A1 | 9/2002 |

OTHER PUBLICATIONS

Carty, E et al., "Thromboxane synthase immunohistochemistry in inflammatory bowel disease", Journal of Clinical Pathology, 2002, pp. 367-370, vol. 55.

Kawakami, M et al., "Roles of thromboxane A2 and leukotriene B4 in radicular pain induced by herniated nucleus pulposus", Journal of Orthopaedic Research, 2001, pp. 472-477, vol. 19.

Lianos, E A et al., "Effect of Thromboxane A2 inhibition and antagonism on prostaglandin and leukotriene synthesis in glomerular immune injury", The Journal of Laboratory and Clinical Medicine, 1999, pp. 478-482, vol. 134, No. 5.

Tozaki, H et al., "Colon-specific delivery of R68070, new thromboxane synthase inhibitor, using chitosan capsules: therapeutic effects against 2,4,6-trinitrobenzene sulfonic acid-induced ulcerative colitis in rats", Life Sciences, 1999, pp. 1155-1162, vol. 64,No. 13.

Al-Maharik, N I, et al., "Synthesis of C-C-Bridged Bis-Isoflavones", Journal Organic Chemistry, 2000, pp. 2305-2308, vol. 65.

Schönberg, A., et. al., "83. Photochemical reactions. Part XV. (a) Photopolymerisation of coumarins and related substances. (b) Photoaddition and reduction processes of aromatic ketones." Journal of the Chemical Society, 1950, pp. 374-379, XP009125900 part (a), compound lb.

Tang, Sharon, et. al., "Biflavonoids with cytotoxic and antibacterial activity from Ochna macrocalyx", Planta Medica, vol. 69, No. 3, 2003, pp. 247-253, XP002555653, compounds 1 and 2.

Supplementary European Search Report issued in counterpart European Patent Application No. 06 72 1277 dated Nov. 26, 2008.

*Primary Examiner*—Bernard Dentz
(74) *Attorney, Agent, or Firm*—Sughrue Mion, PLLC

(57) ABSTRACT

Novel compounds based on phenyl-substituted naphtho[1,2-g]chrysene compounds (A) are described. The compounds are obtainable by dimerisation of 3-phenylchroman (isoflavonoid) ring systems (B). Methods of synthesis of the novel dimeric compounds, compositions containing same and use of the dimers as therapeutic agents are also described.

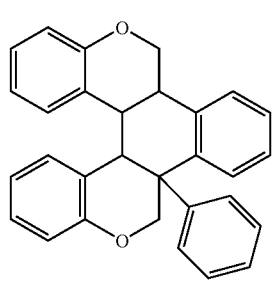

Structure A

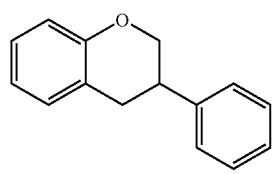

Structure B

18 Claims, 16 Drawing Sheets

A  NV-5063/Doxorubicin Direct Sequence

B  NV-5063/Doxorubicin NV-5063 First Sequence

C  NV-5063/Doxorubicin Doxorubicin First Sequence

ISOFLAVONOID DIMERS

This Application is a 371 of PCT/AU2006/000395, filed Mar. 24, 2006; the disclosure of which is incorporated herein by reference.

Field of the Invention

The present invention generally relates to novel dimeric compounds having a naphtho[1,2-g]chrysene skeleton. The compounds are based on the dimerisation of 3-phenylchroman (isoflavonoid) ring systems. The present invention further relates to the synthesis of the dimeric isoflavonoid compounds, compositions containing same and their use as therapeutic agents. In particular, the dimeric compounds of the present invention are useful in the treatment and prevention of a range of important human disease including cancers, inflammatory disorders, autoimmune disorders, cardiovascular disorders, and disorders associated with estrogen receptor activation.

Background of the Invention

Naturally-occurring plant isoflavones are known to possess a wide range of fundamental biological effects on human cells including anti-oxidation and the up-regulation and down-regulation of a wide variety of enzymes and signal transduction mechanisms. Mitotic arrest and cytotoxicity of human cancer cells, increased capillary permeability, increased cellular adhesion, increased response of vascular smooth muscle cells to vaso-relaxants, and agonism of estrogen receptors, are just a few examples of the responses of animal cells to the biological effects of naturally-occurring isoflavonoids. Some common naturally occurring isoflavones are daidzein, genistein, formononetin, biochanin A, glycitein, coumestrol, daidzin, glycitin and genistin.

Recently, interest has been expressed in the biological properties of dimeric forms of isoflavonoids. Genistein-based dimers have been reported to be 5-alpha-reductase inhibitors useful for the treatment of prostatomegaly [JP 07-224944; publication No. JP 09-067362]. In one form, the dimer results from the joining by a single C—C bond of the 3' position of the genistein pendent phenyl group to the 6 position of the benzopyran ring of the second genistein molecule as follows:

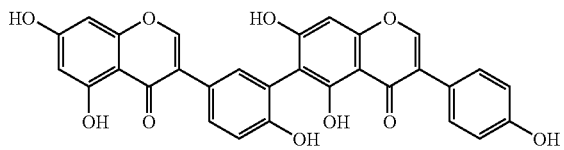

These dimeric compounds can be generally referred to as bis-(3'→6)-isoflavones following from their positions of attachment. Other compounds described are based on genistein and/or daidzein based dimers of the same generic ring structure.

Another dimer is based on a bis-(2→2)-isoflavone structure but having a linker between the two isoflavone molecules as shown below, however no biological activity or therapeutic benefit has been ascribed to it [Al-Maharik N I, Kaltia S A A, Mutikainen I and Wahala K, Synthesis of C—C-Bridged Bis-Isoflavones, *J. Org. Chem.*, 2000, 65, 2305].

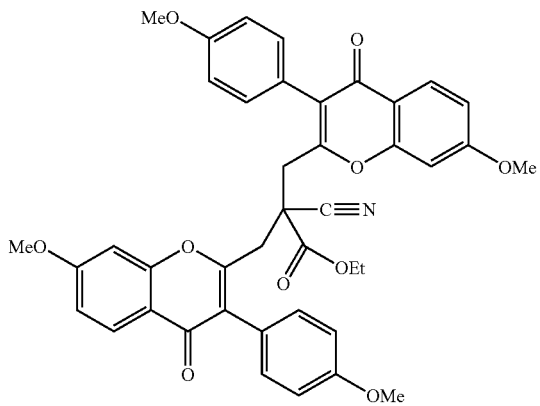

Recently, a further class of dimeric isoflavonoid compounds was discovered exhibiting strong binding affinity for both estrogen receptors and hence showing remarkable physiological activity [WO02/070502]. The lead dimeric compound was a bis-(4→6)-isoflavonoid compound based on dehydroequol as set out below:

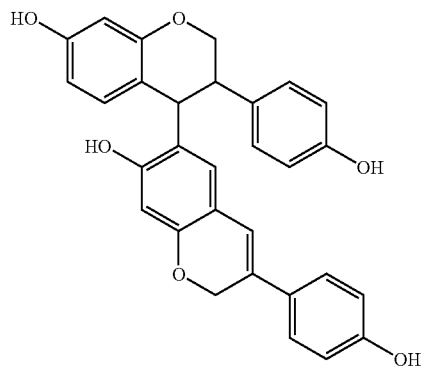

All of these prior art dimeric isoflavonoid compounds are constructed by the joining of two isoflavonoid ring structures by a single carbon-carbon bond, or by a linker or bridging molecule.

Despite the considerable research and accumulated knowledge in relation to isoflavones and derivatives thereof, the full ambit of therapeutically useful isoflavonoid compounds and their activities is yet to be realised. Moreover, there is a continual need for new, improved or at least alternative active agents for the treatment, prophylaxis, amelioration, defense against and/or prevention of various diseases and disorders.

A requirement accordingly exists for new generation compounds that exhibit physiological properties important to the health and well-being of animals, particularly humans, and to find new methods which exploit these properties for the treatment, amelioration and prophylaxis of disease.

SUMMARY OF THE INVENTION

Surprisingly, for the first time, the present inventors have synthesised a new class of dimeric molecules based on isoflavonoid compounds joined by two (2) carbon-carbon single bonds. The skeleton is based on a naphtho[1,2-g]chrysene structure following from bis(4→4) and (2'→3) joining of two 3-phenylchroman ring systems as depicted in generic Structure A below. Dashed lines represent the two C—C bonds formed during dimerisation of the corresponding monomers.

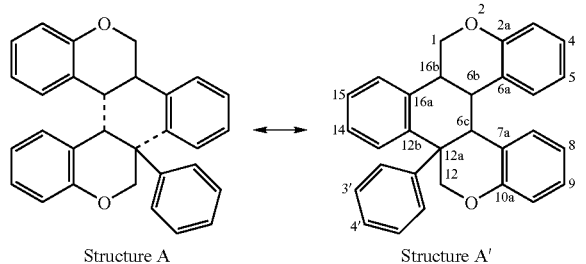

Structure A    Structure A'

The numbering system given above for the 2,11-dioxa-12a-phenyl-(1H,12H)-6b,6c,12a,16b-tetrahydronaphtho[1,2-g]chrysene (Structure A') is used throughout this specification for consistency.

The dimeric molecules of the present invention show promise in their potential use as physiologically active agents and in particular their ability to exhibit binding affinity for the estrogen receptors. Cell line studies have also highlighted the remarkable and unexpected utility of the dimeric isoflavonoid compounds of the present invention as chemotherapeutic agents. The compounds also find use as chemosensitisers, radiosensitisators, antiinflammatory agents and in cardiovascular applications including vasodilation.

Thus according to a first aspect of the present invention there is provided a compound of the general formula (I):

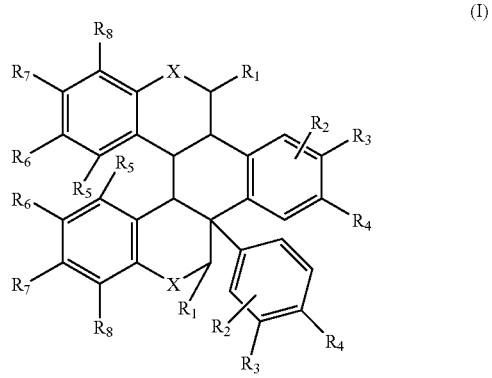

(I)

wherein $R_1, R_2, R_3, R_4, R_5, R_6, R_7$ and $R_8$ are independently hydrogen, hydroxy, $OR_9$, $OC(O)H$, $OC(O)R_9$, $OSi(R_{10})_3$, $C(O)R_{11}$, $CO_2R_{12}$, alkyl, haloalkyl, cycloalkyl, aryl, arylalkyl, thiol, alkylthio, amino, alkylamino, dialkylamino, nitro, cyano or halo, $R_9$ is alkyl, haloalkyl, aryl, arylalkyl or alkylaryl, $R_{10}$ is independently hydrogen, alkyl or aryl, $R_{11}$ is hydrogen alkyl, aryl, arylalkyl or an amino acid, $R_{12}$ is hydrogen, alkyl, haloalkyl, aryl or arylalkyl, and X is O, $NR_{12}$ or S, preferably O, which compounds may be optionally substituted or a pharmaceutically acceptable salt thereof.

According to a second aspect of the present invention there is provided a method for the preparation of a compound of formula (I) which method includes the step of reacting a compound of the formula (II):

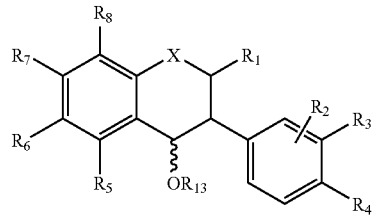

(II)

wherein $R_1, R_2, R_3, R_4, R_5, R_6, R_7$ and $R_8$ are independently hydrogen, hydroxy, $OR_9$, $OC(O)H$, $OC(O)R_9$, $OSi(R_{10})_3$, $C(O)R_{11}$, $CO_2R_{12}$, alkyl, haloalkyl, cycloalkyl, aryl, arylalkyl, thiol, alkylthio, amino, alkylamino, dialkylamino, nitro, cyano or halo, $R_9$ is alkyl, haloalkyl, aryl, arylalkyl or alkylaryl, $R_{10}$ is independently hydrogen, alkyl or aryl, $R_{11}$ is hydrogen alkyl, aryl, arylalkyl or an amino acid, $R_{12}$ is hydrogen, alkyl, haloalkyl, aryl or arylalkyl, $R_{13}$ is hydrogen, $R_9$, $C(O)R_9$, $Si(R_{10})_3$, alkylsulfonyl or benzenesulfonyl, and X is O, $NR_{12}$ or S, preferably O, which compounds may be optionally substituted or a pharmaceutically acceptable salt thereof, with a coupling agent.

In a preferred embodiment, the pendent phenyl ring of the 3-phenyl chroman structure is electron donating and there is at least one ortho hydrogen atom to facilitate formation of the (2→3) bond during dimerisation.

The group $OR_{13}$ is preferably a leaving group selected from halogens such as Cl, Br or I, hydroxy, alkylsulfonyloxy groups such as mesylate and trifluoromethanesulfonyloxy, arylsulfonyloxy groups such as tosylate, mesitylenesulfonyloxy, benzenesulfonyloxy and nitro-substituted benzenesulfonyloxy, acyloxy groups such as acetoxy or benzoyloxy and aryloxy groups such as benzyloxy.

According to a third aspect of the present invention there is provided a method for the treatment, prophylaxis or amelioration of a disease which method includes the step of administering a therapeutically effective amount of one or more compounds of formula (I) to a subject.

According to a fourth aspect of the present invention there is provided the use of one or more compounds of formula (I) in the manufacture of a medicament for the treatment of disease.

According to a fifth aspect of the present invention there is provided the use of one or more compounds of formula (I) as an anti-inflammatory agent, cardiovascular agent, chemotherapeutic agent, chemosensitiser or radiosensitiser.

The inflammatory disorders include inflammatory bowel disease, ulcerative colitis, ulcerative proctitis, distal colitis and Crohn's disease. The compounds are also useful for the treatment of pain associated with inflammation. In a preferred embodiment, the treatment of the inflammatory disorders is absent cardiovascular side effects, cardioprotective and/or is gut protective.

According to a sixth aspect of the present invention there is provided the use of a thromboxane synthase inhibitor for the manufacture of a medicament for the treatment of inflammation, including pain associated with inflammation. Preferably the treatment is cardioprotective and/or gut protective.

According to a seventh aspect of the present invention there is provided an agent for the treatment, prophylaxis or amelioration of a disease which agent comprises one or more compounds of formula (I).

In a preferred embodiment the disease is cancer, a tumour or the unwanted proliferation or upregulation of cellular growth.

According to an eighth aspect of the present invention there is provided a pharmaceutical composition which comprises one or more compounds of formula (I) in association with one or more pharmaceutical carriers and/or excipients.

According to a ninth aspect of the present invention there is provided a drink or food-stuff, which contains one or more compounds of formula (I).

According to a tenth aspect of the present invention there is provided a method of increasing or restoring the sensitivity of cancer cells or a tumour to chemotherapy by contacting said cells or tumour with an isoflavonoid dimer of formula (I). In an embodiment, the chemotherapeutic agent is a growth receptor inhibitor or death receptor stimulator.

According to an eleventh tenth aspect of the present invention there is provided a method of increasing or restoring the sensitivity of cancer cells or a tumour to radiotherapy by contacting said cells or tumour with an isoflavonoid compound of formula (I) as set out below. In another embodiment, the patient is subjected to both chemotherapy and radiotherapy in their treatment regime.

According to a twelfth aspect of the present invention there is provided a method of protecting a non-tumour cell from chemotherapy or radiotherapy, preferably chemotherapy, by contacting the non-tumour cell or a tumour mass with an isoflavonoid dimer of formula (I).

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

DETAILED DESCRIPTION OF THE INVENTION

Figure 1:
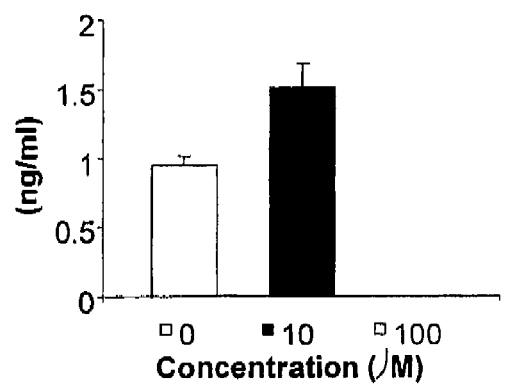
FIG. 1 shows the effect of Cpd. 1 on $PGE_2$ synthesis in human monocytes incubated with LPS.
Figure 1:
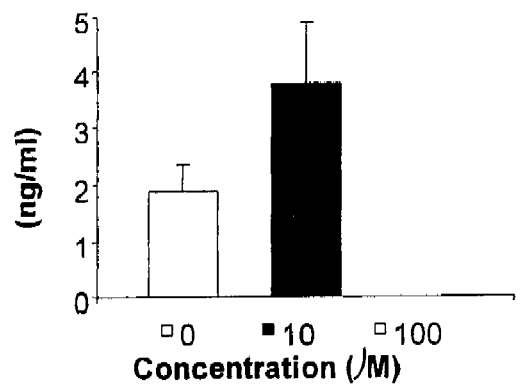
Figure 1:
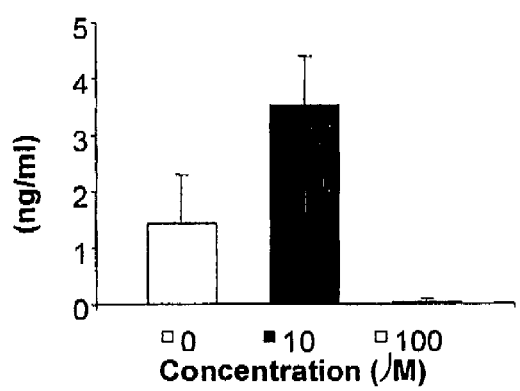
Figure 2:
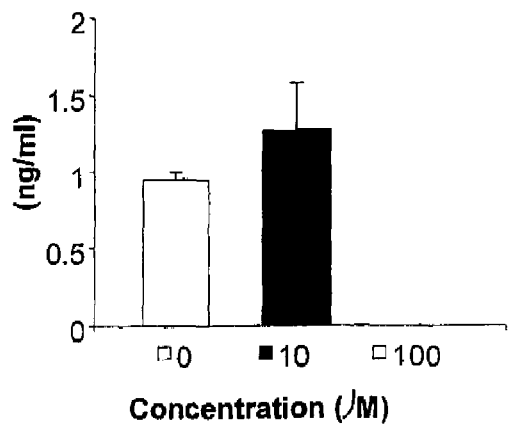
FIG. 2 shows the effect of Cpd. 2 on $PGE_2$ synthesis in human monocytes incubated with LPS.
Figure 2:
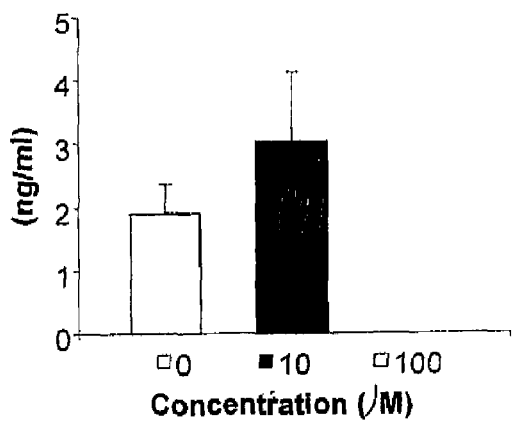
Figure 2:
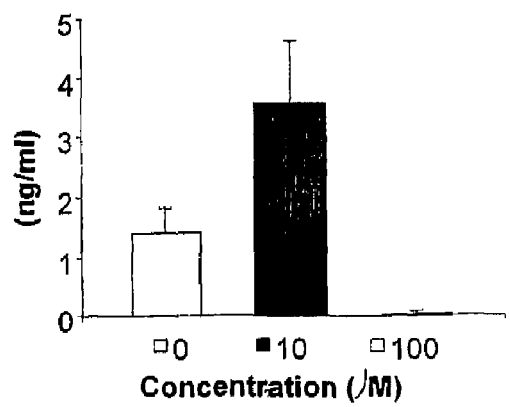
Figure 3:
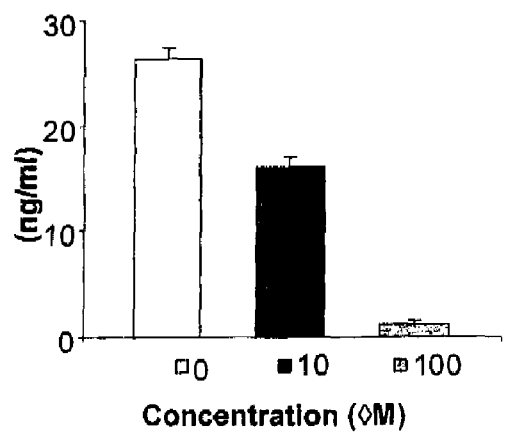
FIG. 3 shows the effect of Cpd. 1 on $TXB_2$ synthesis in human monocytes incubated with LPS.
Figure 3:
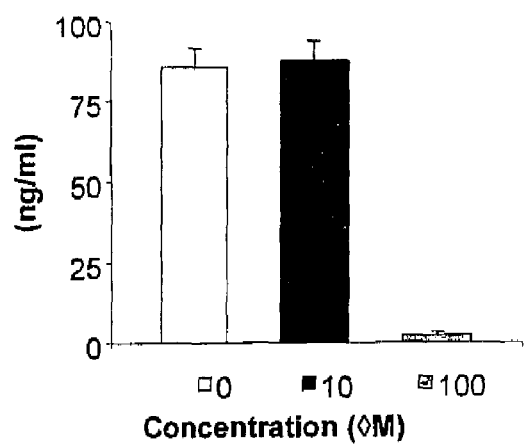
Figure 3:
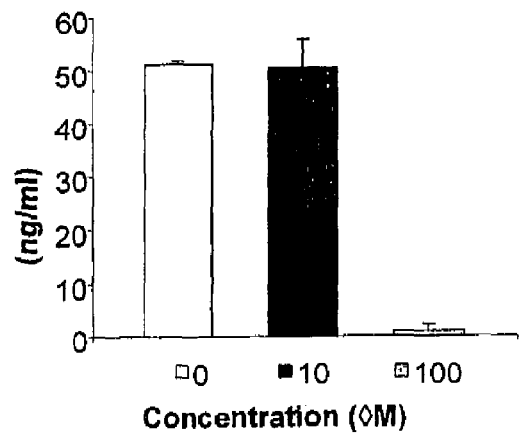
Figure 4:
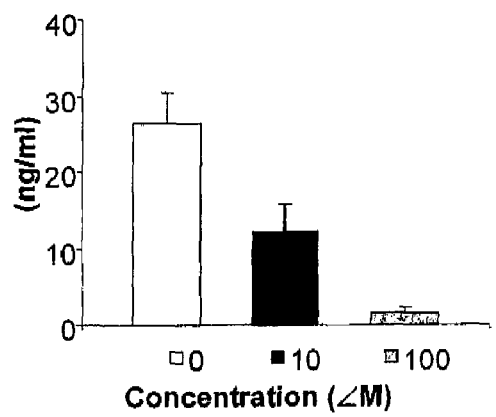
FIG. 4 shows the effect of Cpd. 2 on $TXB_2$ synthesis in human monocytes incubated with LPS.
Figure 4:
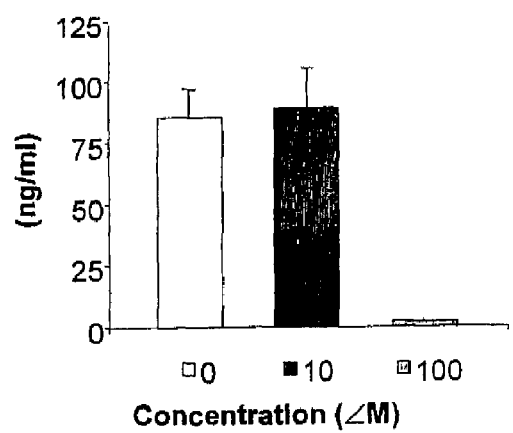
Figure 4:
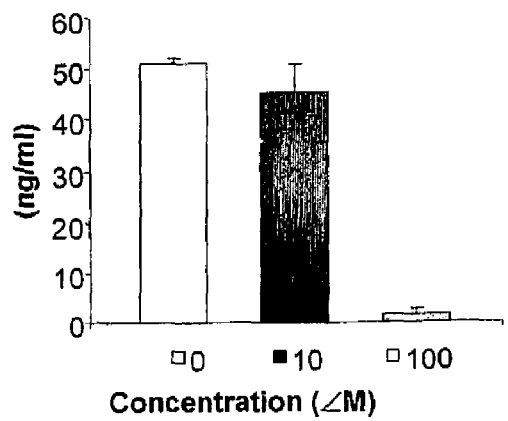
Figure 5:
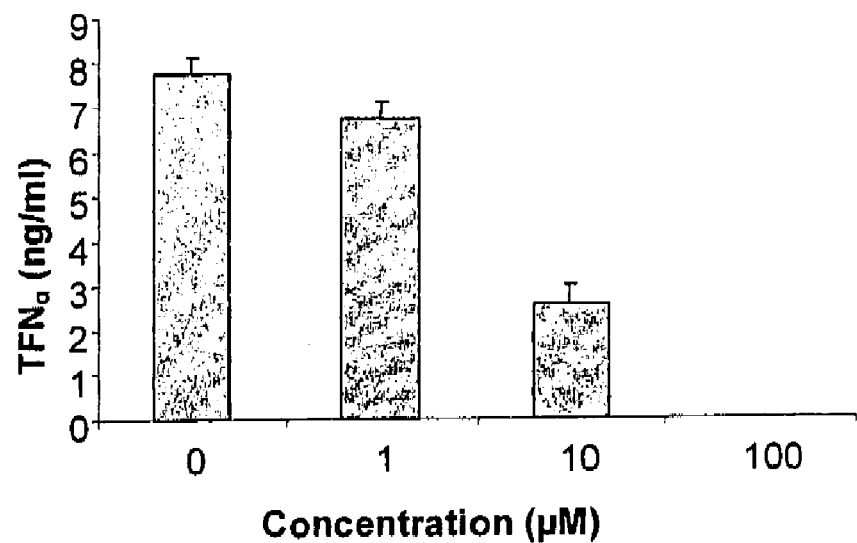
FIG. 5 shows the effect of Cpd. 1 on TNFα synthesis in human monocytes incubated with LPS.
Figure 6:
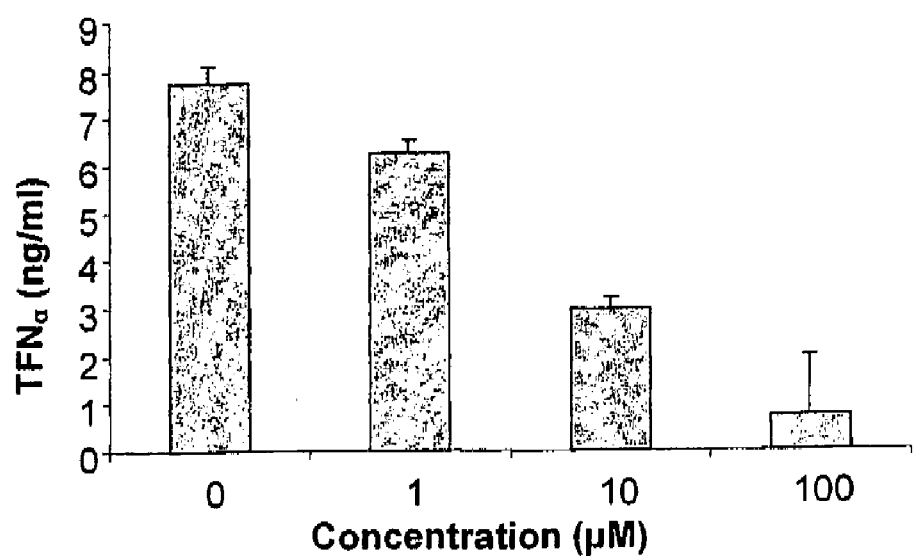
FIG. 6 shows the effect of Cpd. 1 on TNFα synthesis in human monocytes incubated with LPS.
Figure 7:
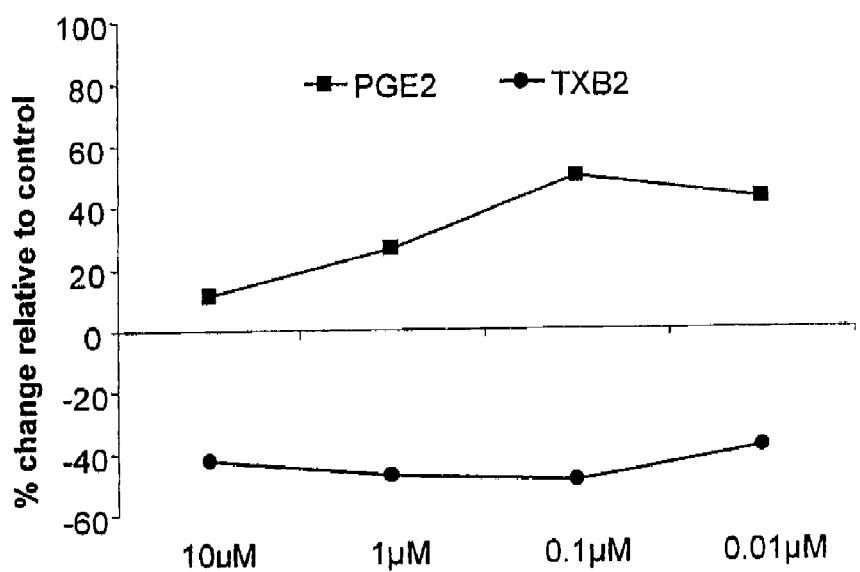
FIG. 7 shows the activity of Cpd. 1 in murine macrophages (RAW 264.7) stimulated with LPS.
Figure 8:
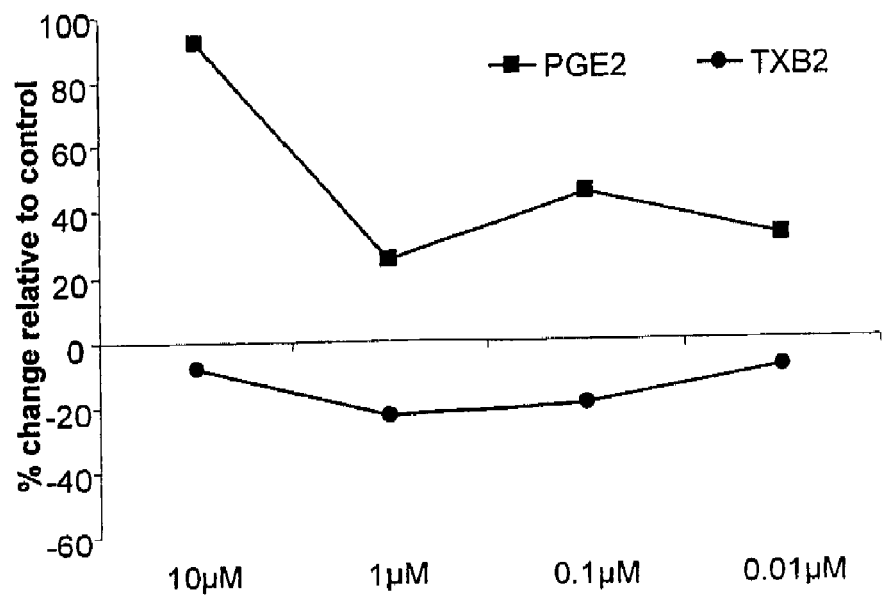
FIG. 8 shows the activity of Cpd. 2 in murine macrophages (RAW 264.7) stimulated with LPS.

The present inventors have found that a class of isoflavonoid dimers of the general formula (I) shows surprising and unexpected biological and pharmaceutical properties.

The compounds of formula (I) of the invention are believed to have favourable toxicity profiles with normal cells and good bioavailability. Surprisingly the compounds of the invention exhibit anti-cancer activity significantly better than or at least comparable to known cancer treatments.

The compounds of formula (I) are cytostatic and cytotoxic against a broad range of cancer cells of human and animal origin. By cancer cells, it is meant cells that display malignant characteristics and which are distinguished from non-cancer cells by unregulated growth and behaviour which usually ultimately is life-threatening unless successfully treated.

The cancer cells that have been found to be responsive to compounds of formula (I) are of epithelial origin (for example, prostate, ovarian, cervical, breast, gall-bladder, pancreatic, colorectal, renal, and non-small lung cancer cells), of neural origin (for example glioma cancer cells) and of mesenchymal origin (for example, melanoma, mesothelioma and sarcoma cancer cells). It is highly unusual and surprising to find a related group of compounds that display such potent cytotoxicity against cancer cells, but with lower toxicity against non-cancer cells such as fibroblasts derived from human foreskin. Such cancer cell selectivity is highly unusual and unexpected.

Advantageously the compounds of formula (I) show cytotoxic activity against cancer cells that are well recognised for being poorly sensitive to standard anti-cancer drugs. It is highly unusual and unexpected to find such potent activity against leukemic cancers.

The invention also provides the use of compounds of formula (I) to treat patients with cancer by either reducing the rate of growth of such tumours or by reducing the size of such tumours through therapy with said compounds alone, and/or in combination with each other, and/or in combination with other anti-cancer agents, and/or in combination with radiotherapy.

The use of compounds of the present invention either alone or in combination therapy as described above may reduce the adverse side-effects often experienced by patients when treated with standard anti-cancer treatments. The use of compounds of the invention may mean that lower doses can be employed in such therapy which represents an important advance for individuals with cancer.

The dimeric molecules of the present invention are structurally related to monomeric isoflavonoid compounds and derivatives thereof. The terms "isoflavone" or "isoflavonoid" as used herein are to be taken broadly to include ring-fused chroman or benzopyran molecules having a pendent phenyl group from the 3-position of the pyran ring. Thus, the classes of compounds generally referred to as isoflavones, isoflavenes, isoflavans, isoflavanones, isoflavanols and the like are generically referred to herein either as isoflavones, isoflavone derivatives or isoflavonoids.

The dimeric molecules of the present invention comprise two carbon-carbon linkages joining the two monomers. The 4-positions on the pyran ring of both isoflavonoid monomers are linked through direct attachment via a carbon-carbon bond. The second linkage joins the 2'-position[#] on the pendant 3-phenyl group of one monomer to the 3-position of the pyran ring of the second isoflavonoid monomer. That is, the methods of the present invention provide simple and direct access to the unique 12a-phenyl naphtho[1,2-g]chrysene ring system of generic Structure A from above.

[#] Depending on the substitution pattern of the pendant phenyl group, the 2'-position might also correctly be referred to as the 6'-position.

Preferred dimeric molecules of the present invention are depicted by the general formula (Ia):

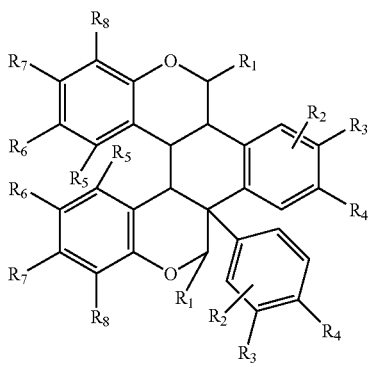

(Ia)

wherein
$R_1$ is hydrogen or $C_{1-6}$-alkyl,
$R_2$, $R_3$ and $R_4$ are independently hydrogen, hydroxy, $OR_9$, $OC(O)R_9$, $OSi(R_{10})_3$, $C_{1-6}$-alkyl, aryl, aryl-$C_{1-6}$-alkyl or halo,
$R_5$, $R_6$, $R_7$ and $R_8$ are independently hydrogen, hydroxy, $OR_9$, $OC(O)R_9$, $OSi(R_{10})_3$, $C_{1-6}$-alkyl, aryl, aryl-$C_{1-6}$-alkyl or halo,
$R_9$ is $C_{1-6}$-alkyl, fluoro-$C_{1-6}$-alkyl or aryl-$C_{1-6}$-alkyl, and
$R_{10}$ is independently $C_{1-6}$-alkyl;

or a pharmaceutically acceptable salt thereof;

more preferably they have the following substituents wherein
$R_1$ is hydrogen,
$R_2$, $R_3$ and $R_4$ are independently hydrogen, hydroxy, $OR_9$, $OC(O)R_9$, $OSi(R_{10})_3$, $C_{1-4}$-alkyl or halo,
$R_5$, $R_6$, $R_7$ and $R_8$ are independently hydrogen, hydroxy, $OR_9$, $OC(O)R_9$, $OSi(R_{10})_3$, $C_{1-4}$-alkyl or halo,
$R_9$ is $C_{1-4}$-alkyl or aryl-$C_{1-4}$-alkyl, and
$R_{10}$ is independently methyl, ethyl or t-butyl, still more preferably they have the following substituents wherein
$R_1$ is hydrogen,
$R_2$, $R_3$ and $R_4$ are independently hydrogen, hydroxy, $OR_9$, $OC(O)R_9$, methyl, ethyl or bromo,
$R_5$, $R_6$, $R_7$ and $R_8$ are independently hydrogen, hydroxy, $OR_9$, $OC(O)R_9$, methyl, ethyl or bromo, and
$R_9$ is methyl, ethyl, propyl, isopropyl or benzyl, or a pharmaceutically acceptable salt thereof.

More highly preferred dimeric molecules of the present invention are depicted by the general formula (Ib):

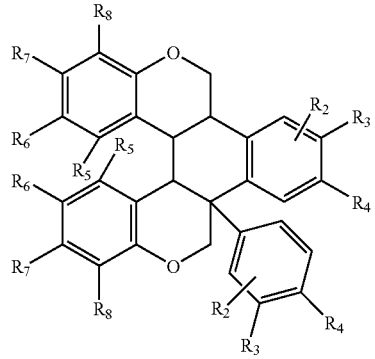

(Ib)

$R_2$, $R_3$, $R_5$, and $R_8$ are independently hydrogen, hydroxy, $OR_9$, $OC(O)R_9$, $OSi(R_{10})_3$, methyl, ethyl, propyl, isopropyl, sec-butyl, t-butyl, phenyl or benzyl,
$R_4$ and $R_7$ are independently hydrogen, hydroxy, $OR_9$, $OC(O)R_9$ or $OSi(R_{10})_3$,
$R_6$ is hydrogen, hydroxy, $OR_9$, $OC(O)R_9$ or $OSi(R_{10})_3$,
$R_9$ is methyl, ethyl, propyl, isopropyl, sec-butyl, t-butyl, phenyl or benzyl, and
$R_{10}$ is independently methyl, ethyl or t-butyl;

most preferably they have the following substituents wherein
$R_2$, $R_3$, $R_5$, and $R_8$ are independently hydrogen, hydroxy, $OR_9$, $OC(O)R_9$ or methyl,
$R_4$ and $R_7$ are independently hydroxy, $OR_9$ or $OC(O)R_9$,
$R_6$ is hydrogen
$R_8$ is hydrogen hydroxy, $OR_9$, $OC(O)R_9$ or methyl, and
$R_9$ is methyl or benzyl.

Still more preferably $R_4$ is methoxy; $R_3$ and $R_4$ are methoxy; and/or $R_8$ is methyl.

Most preferably the novel dimeric compounds of formula I are:
4,9-Dihydroxy-14,15-dimethoxy-12a-(3',4'-dimethoxyphenyl)-2,11-dioxa-(1H,12H)-6b,6c,12a,16b-tetrahydronaphtho[1,2-g]chrysene (1)
4,9-Diacetoxy-14,15-dimethoxy-12a-(3',4'-dimethoxyphenyl)-2,11-dioxa-(1H,12H)-6b,6c,12a,16b-tetrahydronaphtho[1,2-g]chrysene (1-Ac)
4,9-Dihydroxy-14,15-dimethoxy-12a-(3',4'-dimethoxyphenyl)-3,10-dimethyl-2,11-dioxa-(1H,12H)-6b,6c,12a,16b-tetrahydronaphtho[1,2-g]chrysene (2)

4,9-Diacetoxy-14,15-dimethoxy-12a-(3',4'-dimethoxyphenyl)-3,10-dimethyl-2,11-dioxa-(1H,12H)-6b,6c,12a,16b-tetrahydronaphtho[1,2-g]chrysene (2-Ac)

Compounds 1 and 2 and acetoxy derivatives 1-Ac and 2-Ac thereof are depicted by the following structural formulae:

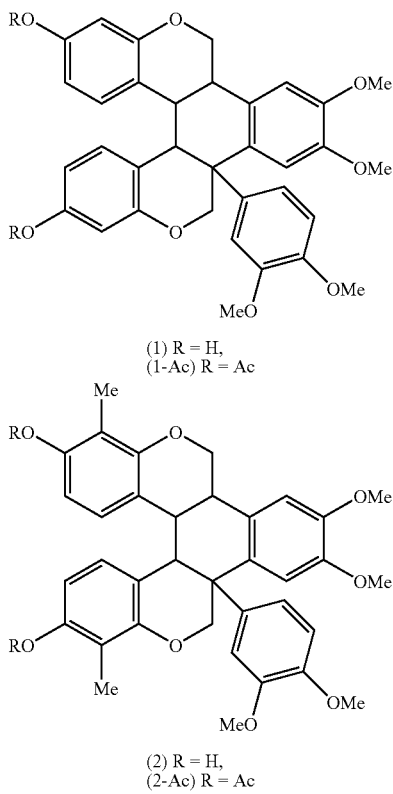

(1) R = H,
(1-Ac) R = Ac (2) R = H,
(2-Ac) R = Ac

Additional preferred compounds were prepared by the same methods with the analogous starting materials. Data was consistent with the products obtained. The compounds are named as follows:

4,9-Dihydroxy-14-methoxy-12a-(4'-methoxyphenyl)-2,11-dioxa-(1H,12H)-6b,6c,12a,16b-tetrahydronaphtho[1,2-g]chrysene (3)

4,9-Diacetoxy-14-methoxy-12a-(4'-methoxyphenyl)-2,11-dioxa-(1H,12H)-6b,6c,12a,16b-tetrahydronaphtho[1,2-g]chrysene (3-Ac)

4,9-Dihydroxy-14-methoxy-12a-(4'-methoxyphenyl)-3,10-dimethyl-2,11-dioxa-(1H,12H)-6b,6c,12a,16b-tetrahydronaphtho[1,2-g]chrysene (4)

4,9-Diacetoxy-14-methoxy-12a-(4'-methoxyphenyl)-3,10-dimethyl-2,11-dioxa-(1H,12H)-6b,6c,12a,16b-tetrahydronaphtho[1,2-g]chrysene (4-Ac)

4,9,14-Trihydroxy-12a-(4'-hydroxyphenyl)-3,10-dimethyl-2,11-dioxa-(1H,12H)-6b,6c,12a,16b-tetrahydronaphtho[1,2-g]chrysene (5)

4,9,14-Triacetoxy-12a-(4'-acetoxyphenyl)-3,10-dimethyl-2,11-dioxa-(1H,12H)-6b,6c,12a,16b-tetrahydronaphtho[1,2-g]chrysene (5-Ac)

4,9-Dihydroxy-15-methoxy-12a-(3'-methoxyphenyl)-2,11-dioxa-(1H,12H)-6b,6c,12a,16b-tetrahydronaphtho[1,2-g]chrysene (6)

4,9-Diacetoxy-15-methoxy-12a-(3'-methoxyphenyl)-2,11-dioxa-(1H,12H)-6b,6c,12a,16b-tetrahydronaphtho[1,2-g]chrysene (6-Ac)

4,9,15-Trihydroxy-12a-(3'-hydroxyphenyl)-3,10-dimethyl-2,11-dioxa-(1H,12H)-6b,6c,12a,16b-tetrahydronaphtho[1,2-g]chrysene (7)

4,9,15-Triacetoxy-12a-(3'-acetoxyphenyl)-3,10-dimethyl-2,11-dioxa-(1H,12H)-6b,6c,12a,16b-tetrahydronaphtho[1,2-g]chrysene (7-Ac)

The term "alkyl" is taken to mean both straight chain and branched chain alkyl groups such as methyl, ethyl, propyl, isopropyl, butyl, isobutyl, secbutyl, tertiary butyl, and the like. The alkyl group has 1 to 10 carbon atoms, preferably from 1 to 6 carbon atoms, more preferable from 1 to 4 carbon atoms, still more preferably methyl, ethyl propyl, isopropyl or t-butyl. The alkyl group may optionally be substituted by one or more of fluorine, chlorine, bromine, iodine, carboxyl, $C_1$-$C_4$-alkoxycarbonyl, $C_1$-$C_4$-alkylamino-carbonyl, di-($C_1$-$C_4$-alkyl)-amino-carbonyl, hydroxyl, $C_1$-$C_4$-alkoxy, formyloxy, $C_1$-$C_4$-alkyl-carbonyloxy, $C_1$-$C_4$-alkylthio, $C_3$-$C_6$-cycloalkyl or phenyl.

The term "aryl" is taken to include phenyl and naphthyl and may be optionally substituted by one or more $C_1$-$C_4$-alkyl, hydroxy, $C_1$-$C_4$-alkoxy, carboxyl, $C_1$-$C_4$-alkoxycarbonyl, $C_1$-$C_4$-alkylcarbonyloxy or halo.

The term "halo" is taken to include fluoro, chloro, bromo and iodo, preferably fluoro, chloro and bromo, more preferably fluoro. Reference to for example "haloalkyl" includes monohalogenated, dihalogenated and up to perhalogenated alkyl groups. Preferred haloalkyl groups are trifluoromethyl and pentafluoroethyl.

The compounds of the invention include all salts, such as acid addition salts, anionic salts and zwitterionic salts, and in particular include pharmaceutically acceptable salts as would be known to those skilled in the art. The term "pharmaceutically acceptable salt" refers to an organic or inorganic moiety that carries a charge and that can be administered in association with a pharmaceutical agent, for example, as a counter-cation or counter-anion in a salt. Pharmaceutically acceptable cations are known to those of skilled in the art, and include but are not limited to sodium, potassium, calcium, zinc and quaternary amine. Pharmaceutically acceptable anions are known to those of skill in the art, and include but are not limited to chloride, acetate, tosylate, citrate, bicarbonate and carbonate.

Pharmaceutically acceptable salts include those formed from: acetic, ascorbic, aspartic, benzoic, benzenesulphonic, citric, cinnamic, ethanesulphonic, fumaric, glutamic, glutaric, gluconic, hydrochloric, hydrobromic, lactic, maleic, malic, methanesulphonic, naphthoic, hydroxynaphthoic, naphthalenesulphonic, naphthalenedisulphonic, naphthaleneacrylic, oleic, oxalic, oxaloacetic, phosphoric, pyruvic, p-toluenesulphonic, tartaric, trifluoroacetic, triphenylacetic, tricarballylic, salicylic, sulphuric, sulphamic, sulphanilic and succinic acid.

The term "pharmaceutically acceptable derivative" or "prodrug" refers to a derivative of the active compound that upon administration to the recipient is capable of providing directly or indirectly, the parent compound or metabolite, or that exhibits activity itself and includes for example phosphate derivatives and sulphonate derivatives. Thus, derivatives include solvates, pharmaceutically active esters, prodrugs or the like. This also includes derivatives with physiologically cleavable leaving groups that can be cleaved in vivo to provide the compounds of the invention or their active moiety. The leaving groups may include acyl, phosphate, sulfate, sulfonate, and preferably are mono-, di- and per-acyl oxy-substituted compounds, where one or more of the pendant hydroxy groups are protected by an acyl group, preferably an acetyl group. Typically acyloxy substituted compounds of the invention are readily cleavable to the corresponding hydroxy substituted compounds.

Synthesis of the isoflavonoid dimers of the present invention conveniently begins with monomeric isoflavan-4-ols of the general formula (II):

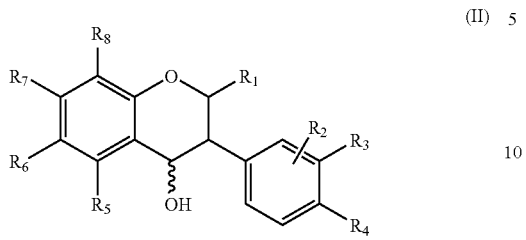
(II)

These starting isoflavan-4-ols or derivatives thereof are readily obtainable by standard procedures known in the art. Published International patent applications WO 98/08503, WO00/49009 and WO 01/17986 (all to Novogen Research Pty Ltd), and references cited therein, which disclosures are incorporated herein by reference, also provide useful synthetic methods for the production of isoflavones, isoflavan-4-ols and related isoflavonoid compounds as the starting monomers. A representative general synthesis is set out in Scheme 1 below.

Scheme 1

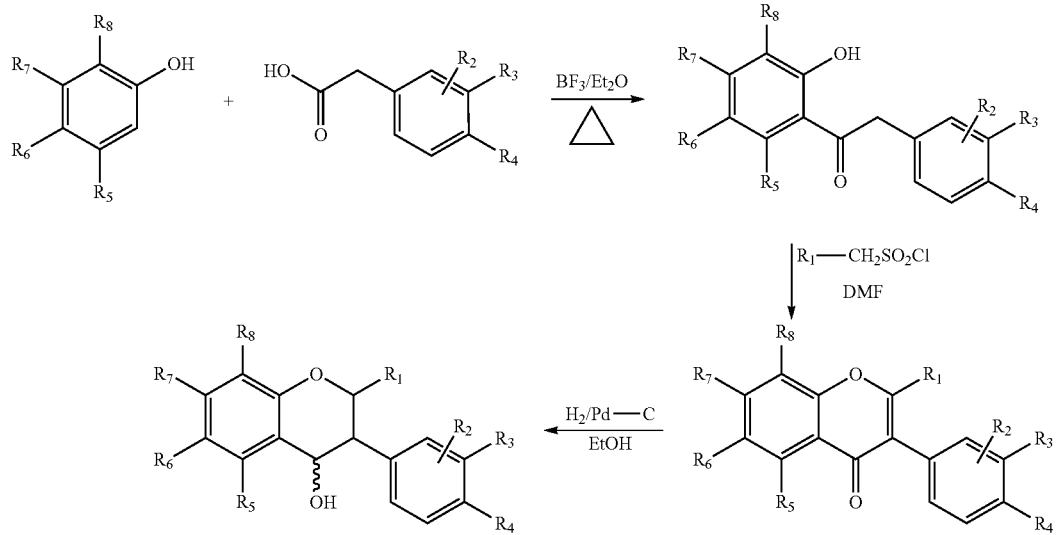

Access to various substitution patterns around both the benzopyran ring and the pendant phenyl ring of the isflavan-4-ols is made possible by selecting correspondingly substituted $R_5$-$R_8$-phenols and $R_2$-$R_4$-phenyl acetic acid starting materials. The ring cyclisation reactions my conveniently be preformed with $R_1$-substituted methanesulfonyl chloride reactants as would be known to those skilled in the art. The reduction reaction is successfully performed with Pd—C or Pd-alumina in an alcoholic solvent in the presence of hydrogen. The person skilled in the art will be aware that other standard methods of alkylation, cyclisation, hydrogenation and/or reduction can be employed as appropriate.

Isoflavan-4-ol monomers are convenient starting materials for the synthesis of the dimeric molecules of the invention.

Dimerisation to yield the naphtho[1,2-g]chrysene derivatives is conveniently performed in the presence of a coupling/dehydration reagent. A representative general synthesis is set out in Scheme 2 below.

Scheme 2

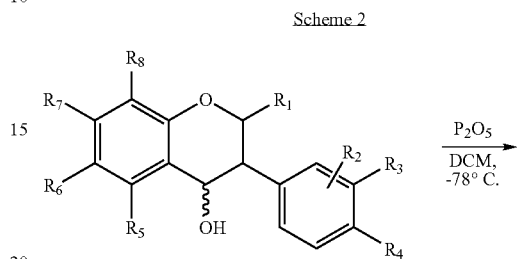

-continued

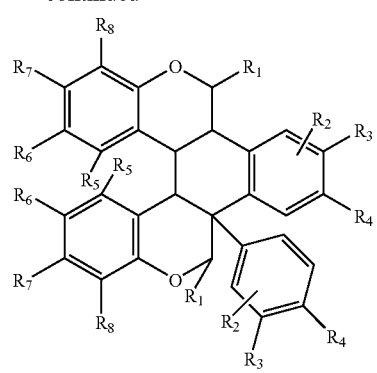

Without wishing to be limited to theory, it is suggested that the reaction proceeds via the formation of an electron-rich olefin (isoflav-3-ene) which quenches a benzylic-stabilised carbocation at the 4-position of the chroman ring on the second monomer. Rearrangement is thought to promote a second carbocation at the 3-position of this second chroman ring, which is then quenched by the 2' (or 6') position of the electron-rich pendent phenyl group. Further rearrangement then affords the resultant dimeric isoflavonoid compounds of the invention. The electron rich phenyl group is preferably a 4- or 2-substituted, 2,4- or 3,4-disubstituted or 2,3,4- or 3,4,5-trisubstituted phenyl group having one or more electron donating groups. The 3,4-disubstituted electron rich compounds are more preferred.

In a preferred embodiment, the coupling agent of choice is phosphorus pentoxide, although the skilled person will understand that other methods and reagents may be employed as appropriate. Such other suitable synthetic methods include Friedel-Crafts alkylation coupling of two isoflavonoids. Typical Friedel-Crafts reaction conditions are obtained with reagents such as aluminium chloride, boron trifluoride or similar Lewis acid catalysts. The coupling reaction is not limited to Friedel-Crafts type conditions, but may include other reaction conditions that can generate a "carbocation" species such as the conversion of a secondary alcohol to a phosphinic ester or similar facile leaving group. Oxidative coupling reaction conditions such as hydrogen peroxide, dilute permanganate, phosphorous pentoxide as noted above or other oxidative compounds may also be employed in the synthesis of the dimeric molecules of the invention.

The dimerisation reactions may be carried out from very low temperatures to ambient, however is it is generally found that lower reaction temperatures promote better yields and cleaner reaction mixtures. The reactions are conveniently performed at −78° C. by way of acetone/dry ice baths.

Solvents suitable for use in the methods of the invention should preferably be liquid at very low temperature, and include the lower chlorinated solvents, THF and acetonitrile. The solvent of choice is dichloromethane. It has been found that a high substrate to solvent ratio is preferred, and the optimal DCM:substrate ratio is about 4:1 for the favoured bimolecular dehydration/cyclisation reactions.

Chemical functional group protection, deprotection, synthons and other techniques known to those skilled in the art may be used where appropriate to aid in the synthesis of the compounds of the present invention, and their starting materials.

The protection of functional groups on the compounds and derivatives of the present invention can be carried out by well established methods in the art, for example as described in T. W. Greene, *Protective Groups in Organic Synthesis*, John Wiley & Sons, New York, 1981.

Hydroxyl protecting groups include but are not limited to carboxylic acid esters, eg acetate esters, aryl esters such as benzoate, acetals/ketals such as acetonide and benzylidene, ethers such as o-benzyl and p-methoxy benzyl ether, tetrahydropyranyl ether and silyl ethers such as t-butyldimethyl silyl ether.

Protecting groups can be removed by, for example, acid or base catalysed hydrolysis or reduction, for example, hydrogenation. Silyl ethers may require hydrogen fluoride or tetrabutylammonium fluoride to be cleaved. Demethylation of methoxy groups provides access to hydroxy-substituted compounds.

The preferred starting isoflavan-4-ol monomers are thought to require electron rich substituents on the isoflavonoid 3-phenyl group for the ready formation of the 2-carbon bond dimers of the present invention. For example, hydroxy (optionally protected) and alkoxy polysubstituted 3-phenyl derivatives are found to be particularly preferred.

The present inventors have surprisingly found that the dimeric molecules of the present invention present a family of new compounds that indicate substantial pharmaceutical promise in the treatment and prevention of a range of important human disease including cancers, inflammatory disorders, autoimmune disorders, cardiovascular disorders and disorders associated with estrogen receptor activation.

In particular, the dimeric compounds of the present invention through their potent ability to inhibit proliferation of cancer cells and to induce apoptosis show use in the prevention and treatment of cancers, a term which any person skilled in the art would understand embraces aberrant growth of both a benign and malignant nature of any or all tissues in the body across epithelial, mesenchymal and neural types. This includes, but is not restricted to, carcinomas, adenocarcinomas, sarcomas, blastomas, adenomas, lymphomas, leukaemias and gliomas.

In particular, the dimeric compounds of the present invention through their potent ability to act as h-ERβ agonists are able to provide oestrogenic support in particular to women of peri-menopausal and menopausal age and to prevent and to treat problems generally recognised as representing acute withdrawal of steroidal estrogen such as vasomotor symptoms (hot flushes and night sweats) and emotional symptoms (anxiety, depression, mood swings), problems generally recognised as representing sub-acute withdrawal of steroidal estrogen such as urinary incontinence and bladder prolapse, and problems generally recognised as representing chronic withdrawal of steroidal estrogen such as osteopaenia and osteoporosis and cognitive dysfunction.

In particular, the dimeric compounds of the present invention through their potent ability to act as h-ERα antagonists are able to prevent or to treat conditions in pre-menopausal women generally regarded as being associated with excessive stimulation of h-ERα receptors and leading to such conditions as cyclic mastalgia, endometriosis, endometrial hyperplasia, uterine fibroids, polycystic ovarian disease and pre-menstrual syndrome.

In particular, the dimeric compounds of the present invention through their potent ability to induce vasodilation and to reduce vasospasm show use in the treatment and prevention of disorders generally recognised as being associated with vasopression either causally or indirectly and embracing but not limited to hypertension and migraine headache.

In particular, the dimeric compounds of the present invention through their potent ability to inhibit inflammatory processes and to moderate immunological processes show use in the prevention and treatment of disorders generally recognised as being associated with excessive inflammation or dysfunctional immune function and embracing but not limited to inflammatory conditions of the gastrointestinal tract including inflammatory bowel disease (including ulcerative colitis and Crohn's disease) sclerosing cholangitis, inflammatory disorders of synovial membranes including rheumatoid arthritis, inflammatory conditions of the respiratory system including asthma as well as autoimmune diseases including glomerulonephritis. The compounds of the invention are also useful in the treatment of pain associated with inflammation. Importantly the compounds are cardioprotective and/or gut protective, thought to be due to their action as a selective thromboxane synthesis inhibitor.

In particular, the dimeric compounds of the present invention through their potent ability to inhibit androgenesis show use in the prevention and treatment of conditions generally recognised as being associated (either causally or indirectly)

with aberrant function of androgens and including but not limited to male pattern baldness (alopecia hereditaria) and prostatic adenoma.

The isoflavanoid dimeric compounds of the invention are also surprisingly active in enhancing the sensitivity of cancer cells to a wide range of anti-cancer treatments (including chemotherapeutic agents and radiation therapy) with vastly different modes of action. The compounds of the invention are also found to restore sensitivity to those same agents in cells that have acquired resistance to those agents and treatment methods.

In a preferred embodiment, the cancer patient is pre-treated with a compound of formula (I) prior to radiotherapy or treatment with a second chemotherapeutic agent. However it is contemplated that any sequence may be used in regard to the administration of a compound of formula (I) and either the radiotherapy or administration of the second chemotherapeutic agent or both.

In a further embodiment the compound of formula (I) is administered after resistance, either inherent or acquired, to radiotherapy is observed in a patient with cancer.

In a further embodiment the compound of formula (I) is administered after resistance, either inherent or acquired, to the chemotherapeutic agent is observed in a patient with cancer.

According to another aspect there is provided a combination therapy comprising administering to a subject undergoing radiotherapy, or about to undergo radiotherapy a therapeutically effective amount of a compound of formula (I). The administration may be sequential or simultaneous or after radioresistance had developed in the subject.

According to another aspect there is provided a combination therapy comprising administering to a subject a therapeutically effective amount of a compound of formula (I) and a chemotherapeutic agent. The administration may be sequential or simultaneous or after chemoresistance had developed in the subject.

In a preferred embodiment, the condition being treated is preferably cancer that is displaying malignant characteristics, but may incorporate earlier stages of cancer such as pre-malignant lesions (eg. atypia, dysplasia, intra-epitelial neoplasia) and benign cancers.

The term "radiotherapy" or radiation therapy" is broadly taken to include methods of treatment or therapy with particles and/or energy waves which affect cancerous cells, tumors or related mechanisms and biological processes. In particular the radiation is a high energy wave or particle such as an X-ray, electron, gamma ray or proton used in radiotherapy, Most preferably the wave or particle is an X-ray.

The term "chemotherapeutic agent" is taken broadly to include all drugs, chemicals, compounds, compositions, agents, drugs, polymers, peptides, proteins and the like which affect cancerous cells, tumors or related mechanisms and biological processes.

The dimeric isoflavonoids of the invention represent a promising new class of chemotherapeutic drugs in the prevention and treatment of cancer. The precise basis of the pharmacological action of these compounds is not fully understood, but the outcome is that of cytostasis and cytotoxicity. Of considerable interest with this family of compounds is that fact that they display broad activity against human and animal cancers, and that they are highly selective for cancer cells.

It has been shown that the dimeric isoflavonoids are potent anti-cancer agents and surprisingly act synergisticly with chemotherapeutics such as cisplatin and gemcitabine, even though these two standard chemotoxic drugs have quite distinct anti-cancer effects within the cell.

More surprisingly the present inventors have found that the isoflavones or derivatives increase or restore the sensitivity of cancer cells and tumors to the effects of radiation therapy.

Treatment regimes may include a single treatment or a course of treatments, called fractions, over several weeks. The fractional treatment is typically given once a day from Monday to Friday, for example, with intermittent rests such as at weekends to help normal cells recover. The actual treatment regime will largely depend on the type of cancer to be treated and the type of radiotherapy to be employed. Those skilled in the art can best determine the most suitable regime for each individual with consideration being given to various factors including the patent's health, progression of disease and type of cancer.

In a preferred embodiment the isoflavones or derivatives thereof are administered prior to radiotherapy. The effect of the pretreatment is to sensitise the cancerous cells or tumors to the effects of the radiation. The isoflavonoid pre-treatment should begin well prior to and/or during the radiotherapy in order to affect the ability of the target cells to resits the radiation. In a broadest preferred embodiment, the pretreatment is for a time and duration sufficient to contact the cancerous cells or tumor with the administered isoflavonoid. This time may typically take 7 days, or 14 days or up to 30 days. In another preferred embodiment the isoflavonoid treatment is 6 days prior to the radiotherapy, or 5 days, or 3 days or 2 days or 1 day prior.

In other circumstances it can be beneficial to administer the isoflavonoids on the day of the radiotherapy which can still have the effect of contributing to cell death by either removing the blockers of apoptosis or to increase the rate of degradation.

Where the treatment includes fractional treatment, the administration of the isoflavonoid may occur at the stated times prior to the first treatment or only some of or each treatment of radiation.

In another preferred embodiment it is found that administration of the isoflavonoids can restore or at least address sensitivity problems which can occur after radiation treatment. In this respect in another preferred embodiment the administration of the isoflavonoids occurs post radiation treatment.

Chemotherapeutic agents are generally grouped as DNA-interactive agents, antimetabolites, tubulin-interactive agents, hormonal agents, other agents such as asparaginase or hydroxyurea. Each of the groups of chemotherapeutic agents can be further divided by type of activity or compound. Chemotherapeutic agents used in combination with the isoflavonoid compound of formula (I) of the present invention, or salts thereof of the present invention, may be selected from any of these groups but are not limited thereto. For a detailed discussion of the chemotherapeutic agents and their method of administration, see Dorr, et al, Cancer Chemotherapy Handbook, 2d edition, pages 15-34, Appleton and Lang (Connecticut, 1994) herein incorporated by reference.

DNA-interactive agents include alkylating agents, e.g. cisplatin, cyclophosphamide, altretamine; DNA strand-breakage agents, such as bleomycin; intercalating topoisomerase II inhibitors, e.g., dactinomycin and doxorubicin); non-intercalating topoisomerase II inhibitors such as, etoposide and teniposide; and the DNA minor groove binder plicamydin, for example.

The alkylating agents form covalent chemical adducts with cellular DNA, RNA, or protein molecules, or with smaller amino acids, glutathione, or similar chemicals. Generally, alkylating agents react with a nucleophilic atom in a cellular constituent, such as an amino, carboxyl, phosphate, or sulfhydryl group in nucleic acids, proteins, amino acids, or in glutathione. The mechanism and the role of these alkylating agents in cancer therapy is not well understood.

Typical alkylating agents include, but are not limited to, nitrogen mustards, such as chlorambucil, cyclophosphamide, isofamide, mechlorethamine, melphalan, uracil mustard; aziridine such as thiotepa; methanesulphonate esters such as busulfan; nitroso ureas, such as carmustine, lomustine, streptozocin; platinum complexes, such as cisplatin, carboplatin; bioreductive alkylator, such as mitomycin, and procarbazine, dacarbazine and altretamine.

DNA strand breaking agents include bleomycin, for example.

DNA topoisomerase II inhibitors include the following intercalators, such as amsacrine, dactinomycin, daunorubicin, doxorubicin (adriamycin), idarubicin, and mitoxantrone; nonintercalators, such as etoposide and teniposide, for example.

A DNA minor groove binder is plicamycin, for example.

Antimetabolites interfere with the production of nucleic acids by one of two major mechanisms. Certain drugs inhibit production of deoxyribonucleoside triphosphates that are the immediate precursors for DNA synthesis, thus inhibiting DNA replication. Certain of the compounds are analogues of purines or pyrimidines and are incorporated in anabolic nucleotide pathways. These analogues are then substituted into DNA or RNA instead of their normal counterparts.

Antimetabolites useful herein include, but are not limited to, folate antagonists such as methotrexate and trimetrexate; pyrimidine antagonists, such as fluorouracil, fluorodeoxyuridine, CB3717, azacitidine, cytarabine, and floxuridine; purine antagonists include mercaptopurine, 6-thioguanine, fludarabine, pentostatin; and ribonucleotide reductase inhibitors include hydroxyurea.

Tubulin interactive agents act by binding to specific sites on tubulin, a protein that polymerizes to form cellular microtubules. Microtubules are critical cell structure units. When the interactive agents bind the protein, the cell can not form microtubules. Tubulin interactive agents include vincristine and vinblastine, both alkaloids and paclitaxel (Taxol), for example.

Hormonal agents are also useful in the treatment of cancers and tumors. They are used in hormonally susceptible tumors and are usually derived from natural sources. Hormonal agents include, but are not limited to, estrogens, conjugated estrogens and ethinyl estradiol and diethylstilbesterol, chlortrianisen and idenestrol; progestins such as hydroxyprogesterone caproate, medroxyprogesterone, and megestrol; and androgens such as testosterone, testosterone propionate; fluoxymesterone, and methyltestosterone.

Adrenal corticosteroids are derived from natural adrenal cortisol or hydrocortisone. They are used because of their anti-inflammatory benefits as well as the ability of some to inhibit mitotic divisions and to halt DNA synthesis. These compounds include, but are not limited to, prednisone, dexamethasone, methylprednisolone, and prednisolone.

Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes.

Antihormonal antigens include, for example, antiestrogenic agents such as tamoxifen, antiandrogen agents such as flutamide; and antiadrenal agents such as mitotane and aminoglutethimide.

Further agents include the following: hydroxyurea appears to act primarily through inhibition of the enzyme ribonucleotide reductase, and asparaginase is an enzyme which converts asparagine to nonfunctional aspartic acid and thus blocks protein synthesis in the tumor.

Preferred chemotherapeutic agents are cisplatin, carboplatin, taxol (paclitaxel), fluorouracil, fluxuridine, cyclophosphamide ifosfamide, hexamethylmelamine, estramustine, mitomycin, and docetaxel.

The amount of one or more compounds of formula I which is required in a therapeutic treatment according to the invention will depend upon a number of factors, which include the specific application, the nature of the particular compound used, the condition being treated, the mode of administration and the condition of the patient. Compounds of formula I may be administered in a manner and amount as is conventionally practised. See, for example, Goodman and Gilman, *The Pharmacological Basis of Therapeutics*, 1299 (7th Edition, 1985). The specific dosage utilised will depend upon the condition being treated, the state of the subject, the route of administration and other well known factors as indicated above. In general, a daily dose per patient may be in the range of 0.1 mg to 2 g; typically from 0.5 mg to 1 g; preferably from 20 mg to 200 mg.

The production of pharmaceutical compositions for the treatment of the therapeutic indications herein described are typically prepared by admixture of the compounds of the invention (for convenience hereafter referred to as the "active compounds") with one or more pharmaceutically or veterinarially acceptable carriers and/or excipients as are well known in the art.

The carrier must, of course, be acceptable in the sense of being compatible with any other ingredients in the formulation and must not be deleterious to the subject. The carrier or excipient may be a solid or a liquid, or both, and is preferably formulated with the compound as a unit-dose, for example, a tablet, which may contain from 0.5% to 59% by weight of the active compound, or up to 100% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, optical, buccal (for example, sublingual), parenteral (for example, subcutaneous, intramuscular, intradermal, or intravenous) and transdermal administration, although the most suitable route in any given case will depend on the nature and severity of the condition being treated and on the nature of the particular active compound which is being used.

Formulation suitable for oral administration may be presented in discrete units, such as capsules, sachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture such as to form a unit dosage. For example, a tablet may be prepared by compressing or moulding a powder or granules containing the active compound, optionally with one or more accessory ingredients. Compressed tablets may be prepared by compressing, in a suitable machine, the compound of the free-flowing, such as a powder or granules optionally mixed with a binder, lubricant, inert diluent, and/or surface active/dispersing agent(s). Moulded tablets may be made by moulding, in a suitable machine, the powdered compound moistened with an inert liquid binder.

Formulations suitable for buccal (sublingual) administration include lozenges comprising the active compound in a flavoured base, usually sucrose and acacia or tragacanth; and pastilles comprising the compound in an inert base such as gelatin and glycerin or sucrose and acacia.

Compositions of the present invention suitable for parenteral administration conveniently comprise sterile aqueous preparations of the active compounds, which preparations are preferably isotonic with the blood of the intended recipient. These preparations are preferably administered intravenously, although administration may also be effected by means of subcutaneous, intramuscular, or intradermal injection. Such preparations may conveniently be prepared by admixing the compound with water or a glycine buffer and rendering the resulting solution sterile and isotonic with the blood. Injectable formulations according to the invention generally contain from 0.1% to 60% w/v of active compound and are administered at a rate of 0.1 ml/minute/kg.

Formulations suitable for rectal administration are preferably presented as unit dose suppositories. These may be prepared by admixing the active compound with one or more conventional solid carriers, for example, cocoa butter, and then shaping the resulting mixture.

Formulations or compositions suitable for topical administration to the skin preferably take the form of an ointment, cream, lotion, paste, gel, spray, aerosol, or oil. Carriers that may be used include Vaseline, lanoline, polyethylene glycols, alcohols, and combination of two or more thereof. The active compound is generally present at a concentration of from 0.1% to 0.5% w/w, for example, from 0.5% to 2% w/w. Examples of such compositions include cosmetic skin creams.

Formulations suitable for transdermal administration may be presented as discrete patches adapted to remain in intimate contact with the epidermis of the recipient for a prolonged period of time. Such patches suitably contain the active compound as an optionally buffered aqueous solution of, for example, 0.1 M to 0.2 M concentration with respect to the said active compound.

Formulations suitable for transdermal administration may also be delivered by iontophoresis and typically take the form of an optionally buffered aqueous solution of the active compound. Suitable formulations comprise citrate or Bis/Tris buffer (pH 6) or ethanol/water and contain from 0.1 M to 0.2 M active ingredient.

Formulations suitable for inhalation may be delivered as a spray composition in the form of a solution, suspension or emulsion. The inhalation spray composition may further comprise a pharmaceutically acceptable propellant such as carbon dioxide or nitrous oxide.

The compositions of the invention may also be administered to a human in a dietary supplement form. Dietary supplements incorporating the actives can be prepared by adding the composition to a food in the process of preparing the food such as by being added to, admixed into, coated, combined or otherwise added to a food stuff. Any food may be used including, but not limited thereto, meats such as ground meats, emulsified meats and marinated meats; beverages such as nutritional beverages, sports beverages, protein fortified beverages, juices, milk, milk alternatives, and weight loss beverages; cheeses such as hard and soft cheeses, cream cheese, and cottage cheese; frozen desserts such as ice cream, ice milk, low fat frozen desserts, and non-dairy frozen desserts; yogurts; soups; puddings; bakery products; salad dressings; and dips and spreads such as mayonnaise, margarine, butter, butter substitute, and other fat containing spreads. The composition is added to the food in an amount selected to deliver a desired dose of the composition to the consumer of the food. Food formulations containing compounds of the invention can be readily prepared according to standard practices.

Therapeutic methods, uses and compositions may be for administration to humans or animals, such as companion and domestic animals (such as dogs and cats), birds (such as chickens, turkeys, ducks), livestock animals (such as cattle, sheep, pigs and goats) and the like.

As used herein, the term "treatment" is to be considered in its broadest context. The term does not necessarily imply that an animal is treated until total recovery. Accordingly, "treatment" includes amelioration of the symptoms or severity of a particular condition or preventing or otherwise reducing the risk of developing a particular condition.

A "pharmaceutically acceptable carrier, excipient, auxiliary and/or diluent" as used herein should be taken to include any carrier, excipient, auxiliary or diluent that is considered useful in preparing a pharmaceutical composition. Such carriers, excipients, auxiliaries or diluents will be generally safe, non-toxic and neither biologically nor otherwise undesirable. The term also includes carriers, excipients, auxiliaries or diluents that are acceptable for veterinary use as well as human pharmaceutical use. As used herein the term "pharmaceutically acceptable carriers, excipients, auxiliaries and/or diluents" includes one of, or more than one of, such substances.

The active compound or pharmaceutically acceptable derivatives prodrugs or salts thereof can also be co-administered with other active materials that do not impair the desired action, or with materials that supplement the desired action, such as antibiotics, antifungals, antiinflammatories, or antiviral compounds. The active agent can comprise two or more isoflavones or derivatives thereof in combination or synergistic mixture. The active compounds can also be administered with lipid lowering agents such as probucol and nicotinic acid; platelet aggregation inhibitors such as aspirin; antithrombotic agents such as coumadin; calcium channel blockers such as verapamil, diltiazem, and nifedipine; angiotensin converting enzyme (ACE) inhibitors such as captopril and enalapril, and β-blockers such as propanolol, terbutalol, and labetalol. The compounds can also be administered in combination with nonsteriodal antiinflammatories such as ibuprofen, indomethacin, aspirin, fenoprofen, mefenamic acid, flufenamic acid and sulindac. The compounds can also be administered with corticosteroids or an anti-emetic such as zofran.

Compounds of formula (I) seem to be particularly suitable for co-administration with other anti-cancer drugs such as gemcitabine, doxorubicin, cisplatin, paclitaxol and/or dehydroequol (DHE). This may result in improved effects in the treatment in comparison to when only one of the medicaments is employed.

The co-administration may be simultaneous or sequential. Simultaneous administration may be effected by the compounds being in the same unit dose, or in individual and discrete unit doses administered at the same or similar time. Sequential administration may be in any order as required and typically will require an ongoing physiological effect of the first or initial active agent to be current when the second or later active agent is administered, especially where a cumulative or synergistic effect is desired.

The invention is further described with reference to the following non-limiting examples.

EXAMPLES

Condensation Reactions

Example 1.1

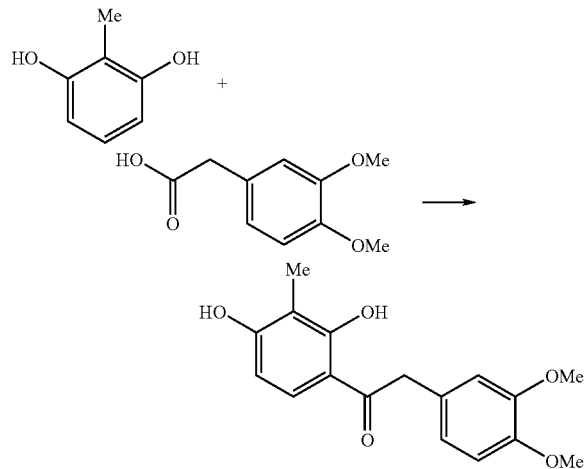

2-Methyl resorcinol (62.2 g) and 3,4-methoxyphenyl acetic acid (92.3 g) were dried over $P_2O_5$ for 4 days. Boron trifluoride diethyl etherate (350 mL) was added to the solids in a round bottom flask and the mixture was stirred under nitrogen with heating to 100° C. for 100 min. The solution was cooled to room temperature for 2 hours and the resulting precipitate was collected and washed with an excess of water to afford 1-(2,4-dihydroxy-3-methylphenyl)-2-(3,4-dimethoxyphenyl)-ethanone as a brown solid (93 g, 65%).

Example 1.2

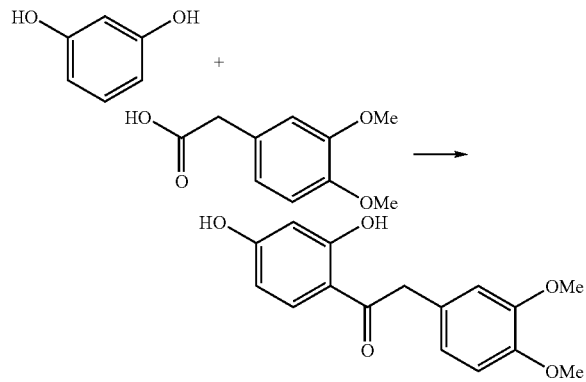

In a similar manner to Example 1.1 above, resorcinol and 3,4-methoxyphenyl acetic acid were dried then reacted in the presence of boron trifluoride diethyl etherate to afford 1-(2,4-dihydroxyphenyl)-2-(3,4-dimethoxyphenyl)ethanone. Other condensation products are obtainable from using the appropriately substituted precursor compounds.

Cyclisation Reactions

Example 2.1

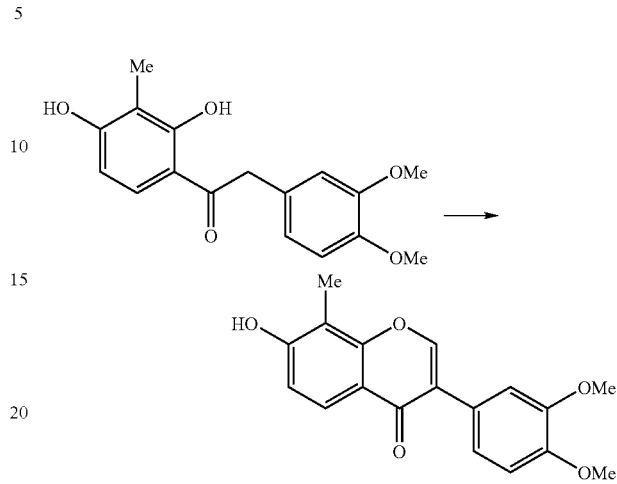

1-(2,4-Dihydroxy-3-methyl-phenyl)-2-(3,4-dimethoxyphenyl)-ethanone (92.9 g) dissolved in DMF (140 mL, dried over $MgSO_4$ for 15 min) was placed under a nitrogen atmosphere. Distilled boron trifluoride diethyl etherate was added (140 mL) over 40 min to the stirred solution at room temperature. A solution of methanesulfonyl chloride (75 mL) in DMF (190 mL) was added at 52-55° C. over 20 min during which the reaction mixture changed to a yellow colour. The reaction was heated to reflux for 80 min and was monitored by HPLC after which it was then left to cool to room temperature.

The dark brown solution was poured into cold, vigorously stirred water (3×1250 mL portions). Overnight (with continued stirring) the yellow solid precipitated out. The solid was washed with water and collected by filtration. The solid was dried to yield 3-(3,4-dimethoxy-phenyl)-7-hydroxy-8-methyl-chromen-4-one as a yellow solid (94.8 g, 99%).

Example 2.2

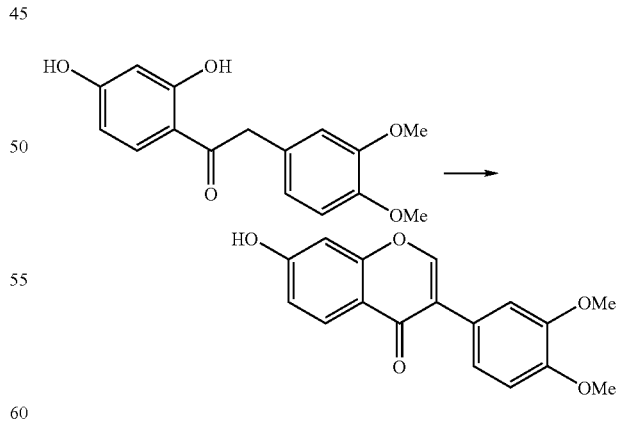

In a similar manner to Example 2.1 above, 1-(2,4-dihydroxyphenyl)-2-(3,4-dimethoxy-phenyl)-ethanone dissolved in DMF had added boron trifluoride diethyl etherate followed by methanesulfonyl chloride in DMF. Addition of water to the reaction mixture afforded 3-(3,4-dimethoxyphenyl)-7-hydroxychromen-4-one.

Acetylation Reactions

Example 3.1

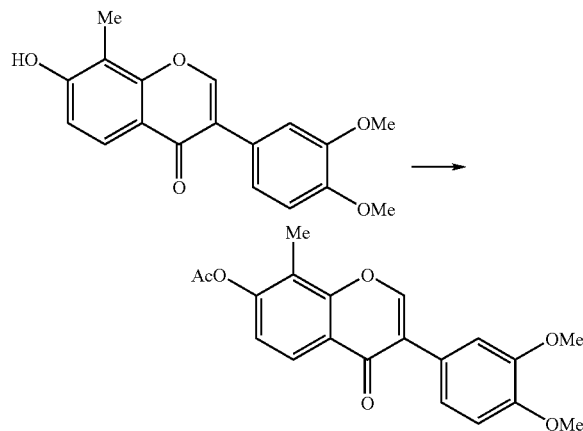

3-(3,4-Dimethoxy-phenyl)-7-hydroxy-8-methylchromen-4-one (94.8 g) was suspended in acetic anhydride (450 mL) under a nitrogen atmosphere. Pyridine (23 mL) was added and the reaction mixture was heated to reflux for 1 hour. The pot was cooled overnight at −18° C. to produce a crystalline solid within the reaction mixture. This was filtered and the solid was washed with the filtrate and additional water (500 mL) to yield a brown solid. Further washing with ethanol produced a white crystalline solid. The solid was dried overnight in a desiccator to yield 7-acetoxy-3-(3,4-dimethoxyphenyl)-8-methylchromen-4-one (44.7 g, 42%).

$^1$H NMR (CDCl$_3$): δ 2.32 (s, 3H, CH$_3$), 2.39 (s, 3H, OCOCH$_3$), 3.92 and 3.93 (each s, 3H, OCH$_3$), 6.93 (d, 1H, J 8.3 Hz, ArH), 7.06 (dd, 1H, J 1.9 Hz 8.3 Hz, ArH), 7.13 (d, 1H, J 8.6 Hz, ArH), 7.22 (d, 1H, J 1.9 Hz, H8), 8.07 (s, 1H, H2), 8.33 (d, 2H, J 8.6 Hz, ArH).

Example 3.2

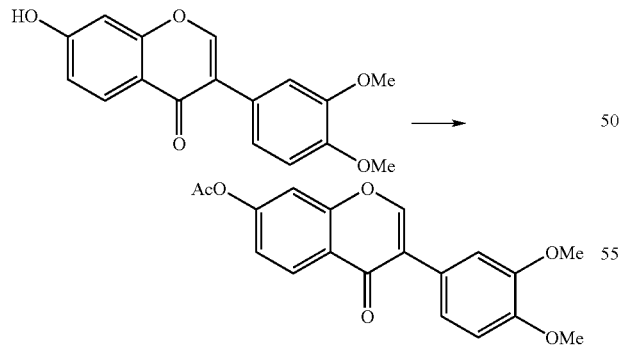

In a similar manner to Example 3.1 above, 3-(3,4-dimethoxyphenyl)-7-hydroxychromen-4-one (1.7 g) was reacted with acetic anhydride (10 ml) and pyridine (1.9 ml) to give 7-acetoxy-3-(3,4-dimethoxyphenyl)chromen-4-one as colourless prisms (1.44 g, 74%).

$^1$H NMR (CDCl$_3$): δ 2.36 (s, 3H, OCOCH$_3$), 3.92 and 3.93 (each s, 3H, OCH$_3$), 6.93 (d, 1H, J 8.3 Hz, ArH), 7.06 (dd, 1H, J 1.9 Hz 8.3 Hz, ArH), 7.16 (d, 1H, J 1.9 Hz, H8), 7.20 (m, 1H, ArH), 7.31 (d, 1H, J 1.9 Hz, ArH), 8.00 (s, 1H, H2), 8.33 (d, 1H, J 8.7 Hz, ArH).

Hydrogenation Reactions

Example 4.1

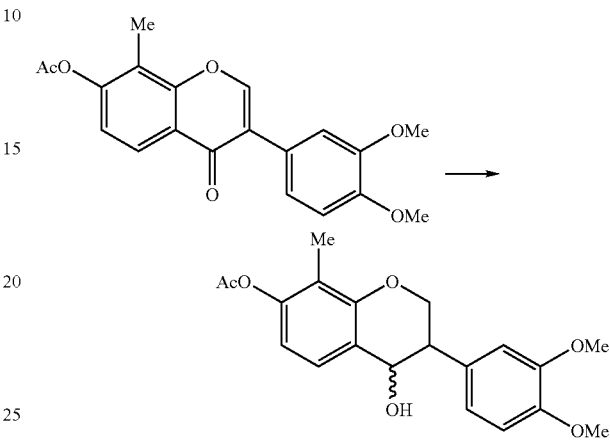

In a 1 L 3N round-bottomed hydrogenation flask, 7-acetoxy-3-(3,4-dimethoxyphenyl)-8-methylchromen-4-one (13.9 g) and Pd/Al$_2$O$_3$ (2.8 g) were suspended in absolute ethanol (560 mL). Hydrogen was introduced to the system for 42 h until the reaction was complete. The reaction mixture was separated by filtration with Celite. The solvent was removed in vacuo to give a white solid which was dried overnight on a high-vacuum line yielding 7-acetoxy3-(3,4-dimethoxyphenyl)-8-methylchroman-4-ol as a mixture of cis- and trans-isomers (9.56 g, 68%). This mixture was used in the next step without any further purification.

trans-isomer: $^1$H NMR (CDCl$_3$): δ 2.02 (s, 3H, CH$_3$), 2.32 (s, 3H, OCOCH$_3$), 3.10 (ddd, 1H, H3), 3.84 and 3.86 (each s, 3H, OCH$_3$), 4.24 (dd, 1H, H2a); 4.39 (dd, 1H, H2b), 4.91 (d, 1H, J 7.9 Hz, 144), 6.50-6.90 (m, 4H, ArH), 7.32 (d, 1H, J 8.7 Hz, H5). cis-isomer: $^1$H NMR (CDCl$_3$): δ 2.03 (s, 3H, CH$_3$), 2.32 (s, 3H, OCOCH$_3$), 3.30 (dt, 1H, H3), 3.86 and 3.87 (each s, 3H, OCH$_3$), 4.31 (ddd, 1H, H2a); 4.54 (dd, 1H, H2b, 4.78 (bd, 1H, H4), 6.50-6.90 (m, 4H, ArH), 7.32 (d, 1H, J 8.3 Hz, H5).

Example 4.2

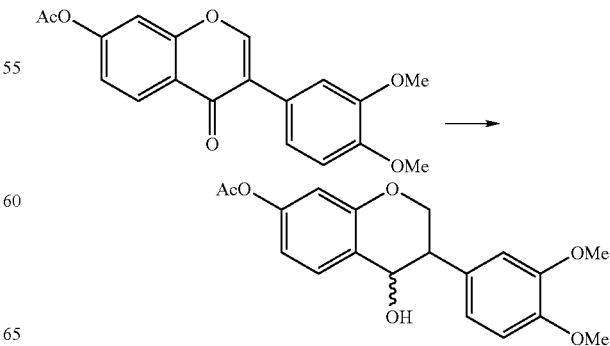

In a similar manner to Example 4.1, 7-acetoxy-3-(3,4-dimethoxyphenyl)chromen-4-one (1.4 g) and 5% Pd—C (0.24 g) were suspended in absolute ethanol (200 mL) and hydrogen was introduced to the system for 55 h until the reaction was complete. Filtration and evaporation gave a cis- and trans-mixture of 7-acetoxy-3-(3,4-dimethoxyphenyl)chroman-4-ol (1.4 g, 100%). This mixture was used in the next step without any further purification.

trans-isomer: $^1$H NMR (CDCl$_3$): δ 2.29 (s, 3H, OCOCH$_3$), 3.14 (ddd, 1H, J 3.4 Hz, J 7.9 Hz, J 8.7 Hz, H3), 3.87 and 3.88 (each s, 3H, OCH$_3$), 4.24 (dd, 1H, H2a); 4.35 (dd, 1H, H2b), 4.93 (d, 1H, J 7.9 Hz, H4), 6.66-6.87 (m, 5H, ArH), 7.49 (d, 1H, J 8.7 Hz, H5). cis-isomer: $^1$H NMR (CDCl$_3$): δ 2.29 (s, 3H, OCOCH$_3$), 3.30 (dt, 1H, H3), 3.87 and 3.88 (each s, 3H, OCH$_3$), 4.31 (ddd, in, H2a); 4.56 (dd, 1H, H2b), 4.75 (d, 1H, J 2.64 Hz, H4), 6.66 (dd, 1H, J 2.3 Hz, J 8.7 Hz, H6), 6.66-6.87 (m, 5H, ArH), 7.30 (d, 2H, J 8.3 Hz, ArH).

Dimerisation Reactions

Example 5.1

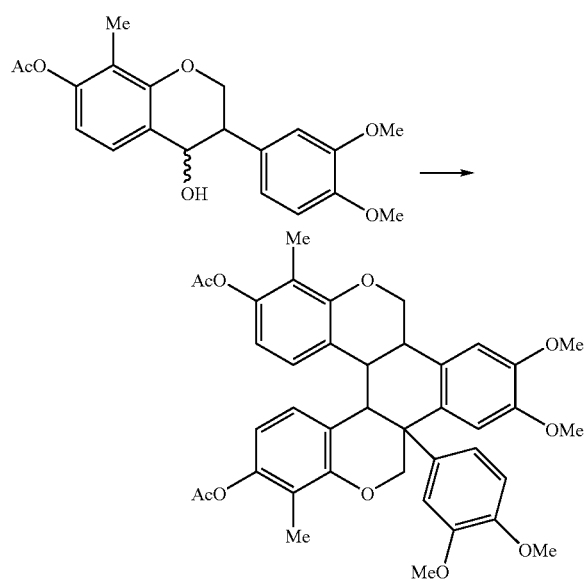

Method A

7-Acetoxy-3-(3,4-dimethoxyphenyl)-8-methylchroman-4-ol (1.08 g) was dissolved in dichloromethane (4 mL) and dried over potassium carbonate. The reaction mixture was cooled to −78° C. (acetone/dry ice bath) for 10 minutes. Phosphorus pentoxide (0.563 g) was added and the reaction was stoppered and kept at −78° C. for 6 hours then stirred at 4° C. overnight. It was quenched using sodium hydrogen carbonate solution (20 mL, 5% w/v) which caused the reaction mixture to bubble. The mixture was rinsed into a separating funnel and the dichloromethane layer was collected. The aqueous layer was extracted using more dichloromethane (~20 mL). The dichloromethane layer was reduced on a Rotovap and formed a purple solid once put on the high vacuum line. The solid was dissolved in eluent and subjected to column chromatography using (60:40) dichloromethane/light petroleum with monitoring by TLC. The product 4,9-diacetoxy-14,15-dimethoxy-12a-(3',4'-dimethoxyphenyl)-3,10-dimethyl-2,11-dioxa-(1H,12H)-6b,6c,12a,16b-tetrahydronaphtho[1,2-g]chrysene (2-Ac) was isolated (580 mg, 52%).

$^1$H NMR (CDCl$_3$); δ 1.86 (s, 3H, CH$_3$), 2.02 (s, 3H, CH$_3$), 2.23 (s, 3H, OCOCH$_3$), 2.30 (s, 3H, OCOCH$_3$), 3.12 (dt J 3.5 Hz, J 11.4 Hz, 1H, CH), 3.36 (d, J 12.2 Hz, 1H, CH), 3.74, 3.83, 3.87, 3.87 (each s, 3H, OCH$_3$), 3.93 (dd, J 3.2 Hz, J 10.8 Hz, 1H, CHa), 4.25 (s, 1H, CH), 4.59 (d, J 11.3 Hz, CHa'), 4.77 (d, J 11.3 Hz, CHb'), 4.88 (dd, J 3.4 Hz, J 10.2 Hz, 1H, CHb), 6.30 (d, 1H, J 8.7 Hz, 1H, ArH), 6.46-6.8 (m, 6H, ArH), 6.93 (s, 1H, ArH), 7.13 (d, 1H, J 8.6 Hz, ArH). $^{13}$C NMR (CDCl$_3$); δ 9.2, 9.3 (CH$_3$), 20.6, 20.7 (CH$_3$), 32.9 (CH), 36.6 (CH), 42.9 (CH), 47.0 (aliphatic C), 55.7, 56.0, 56.2, 56.3 (OCH$_3$), 70.0 (CH$_2$), 72.8 (CH), 108.4, 111.2, 111.3, 112.2, 113.8, 113.9, 120.2, 123.3, 125.7 (Ar CH), 118.5, 118.9, 120.5, 121.9, 128.7, 129.2, 138.4, (ArC), 147.9, 148.0, 148.1, 148.2, 148.3, 148.9, 153.5, 154.2 (ArC), 169.2, 169.3 (COOCH$_3$). λ$_{max}$ 285 nm (ε 14,310). ν$_{max}$ 2932, 1759, 1597, 1516, 1428, 1368, 1217, 1093, 1024, 912, 805, 729, 587 cm$^{-1}$. Found: (HRESMS) m/z 703.254039; C$_{40}$H$_{40}$O$_{10}$Na requires m/z 703.251343.

Method B

Four 20 mL reaction vessels were set up according to Table 1 below by combining the two solids and cooling them to −78° C. in an acetone/dry ice bath for 10 minutes.

TABLE 1

Reaction vessels of 7-acetoxy-3-(3,4-dimethoxyphenyl)-8-methylchroman-4-ol monomer, P$_2$O$_5$ and DCM.

| Flask # | Monomer (g) | P$_2$O$_5$ (g) | Dichloromethane (mL) |
|---|---|---|---|
| 1 | 1.0037 | 0.5387 | 4 |
| 2 | 1.0156 | 0.4433 | 4 |
| 3 | 1.0094 | 0.4490 | 4 |
| 4 | 1.0101 | 0.6348 | 4 |

Dichloromethane dried over potassium carbonate was chilled to −78° C. and added slowly to the flasks. The reaction mixtures were kept at −78° C. for 6-7 hours, then quenched using sodium hydrogen carbonate solution (20 mL, 5% w/v) which caused the reaction mixture to bubble. The reactions were combined and transferred to a separating funnel and the dichloromethane layer was collected. The aqueous layer was extracted using dichloromethane (~20 mL). The dichloromethane layer was reduced on a Rotovap and the residue formed a purple solid once dried on a high vacuum line. The solids were then subjected to column chromatography using (60:40) dichloromethane/light petroleum. The diacetoxy dimer was successfully isolated from the latter fractions (1085 mg, 26%).

Example 5.2

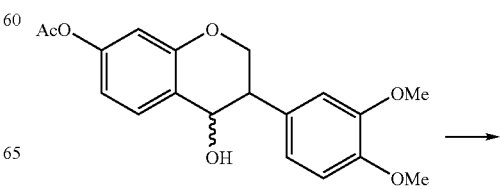

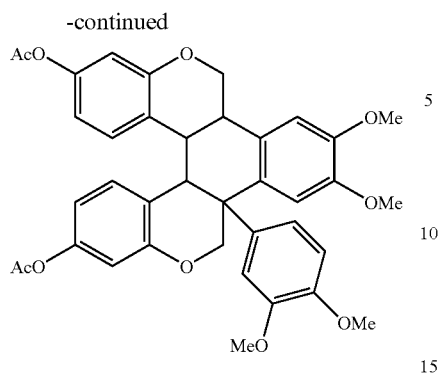

In a similar manner to Method A of Example 5.1, 7-acetoxy-3-(3,4-dimethoxyphenyl)chroman-4-ol in dichloromethane was treated with phosphorus pentoxide to afford 4,9-diacetoxy-14,15-dimethoxy-12a-(3',4'-dimethoxyphenyl)-2,11-dioxa-(1H,12H)-6b,6c,12a,16b-tetrahydronaphtho[1,2-g]chrysene (1-Ac) (54%).

$^1$H NMR (CDCl$_3$): δ 2.20 (s, 3H, OCOCH$_3$), 2.27 (s, 3H, OCOCH$_3$), 3.09 (dt, J 3.8 Hz, J 11.7 Hz, 1H, CH), 3.36 (d, J 12.5 Hz, 1H, CH), 3.74, 3.84, 3.89, 3.89 (each s, 3H, OCH$_3$), 3.95 (dd, 33.4 Hz, J 10.9 Hz, 1H, CHa), 4.23 (s, 1H, CH), 4.59 (d, J 11.3 Hz, CHa'), 4.73 (d, 11.3 Hz, CHb'), 4.81 (dd, J 3.4 Hz, 10.9 Hz, 1H, CHb), 6.36 (dd, 1H, J 2.6 Hz, J 8.7 Hz, 1H, ArH), 6.46 (d, J 2.3 Hz, 1H, ArH), 6.62 (d, J 2.3 Hz, 1H, ArH), 6.62-6.69 (m, 4H, ArH), 6.79 (d, J 9.1 Hz, 1H, ArH), 6.85 (d, J 8.7 Hz, 1H, ArH), 6.91 (s, 1H, ArH), 7.24 (d, 1H, J 9.0 Hz, ArH). $^{13}$CNMR (CDCl$_3$): δ 21.5, 21.6 (CH$_3$), 33.5 (CH), 36.8 (CH), 43.1 (CH), 49.9 (aliphatic C), 56.2, 56.3, 56.4, 56.5 (OCH$_3$), 70.5 (CH$_2$), 73.2 (CH$_2$), 108.7, 110.7, 110.8, 11.5, 112.4, 114.4, 120.8, 120.9, 126.9, 129.2, 129.3 (ArCH), 122.6, 128.8, 138.4, 148.4, 148.5, 148.6, 149.3, 150.1, 150.3, 155.8, 156.3, 169.7, 169.8 (ArC). λ$_{max}$ 284 nm (ε 18,000), 212 (77250). ν$_{max}$ 2993, 2833, 1762, 1611, 1586, 1516, 1464, 1424, 1368, 1248, 1209, 1146, 1119, 1027, 899, 810, 763 cm$^{-1}$. Found: (HRESMS) m/z 675.219688; C$_{38}$H$_{36}$O$_{10}$Na requires m/z 675.220045.

Deacetylation Reactions

Example 6.1

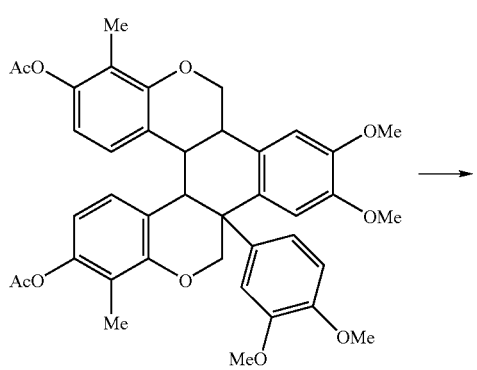

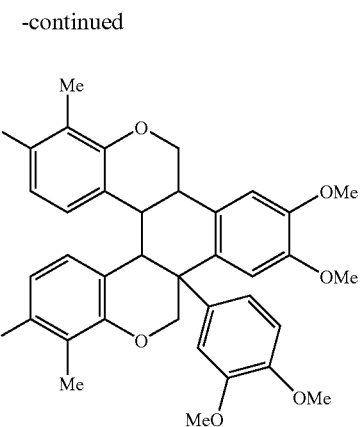

4,9-Diacetoxy-14,15-dimethoxy-12a-(3',4'-dimethoxyphenyl)-3,10-dimethyl-2,11-dioxa-(1H,12H)-6b,6c,12a,16b-tetrahydronaphtho[1,2-g]chrysene (150 mg) was dissolved in methanol (4 ml). Potassium hydroxide solution (1M aqueous) was added dropwise to the reaction until the pH was approximately 11. The reaction was stirred for 90 minutes at room temperature. The solution was neutralised with acetic acid (1M aqueous) and poured into stirred water (500 ml). The resulting precipitate was filtered and dried yielding a white powder identified as 4,9-dihydroxy-14,15-dimethoxy-12a-(3',4'-dimethoxyphenyl)-3,10-dimethyl-2,11-dioxa-(1H,12H)-6b,6c,12a,16b-tetrahydronaphtho[1,2-g]chrysene (2) (50 mg, 38%).

$^1$H NMR (CDCl$_3$); δ 1.94 (s, 3H, CH$_3$), 2.10 (s, 3H, CH$_3$), 3.02 (dt J 3.5 Hz, J 11.4 Hz, 1H, CH), 3.31 (d, J 12.4 Hz, 1H, CH), 3.74, 3.84, 3.86, 3.87 (each s, 3H, OCH$_3$), 3.94 (dd, J 3.2 Hz, J 10.8 Hz, 1H, CHa), 4.18 (s, 1H, CH), 4.40 (brs, 1H, OH), 4.56 (d, J 11.3 Hz, 1H, CHa'), 4.60 (brs, 1H, OH), 4.74 (d, J 11.3 Hz, 1H, CHb'), 4.86 (dd, J 3.4 Hz, J 10.2 Hz, 1H, CHb), 6.10 (d, J 8.7 Hz, 1H, ArH), 6.42 (d, J 8.7 Hz, 1H, ArH), 6.59 (d, J 8.7 Hz, 1H, ArH), 6.60-6.8 (m, 3H, ArH), 6.79 (d, J 8.7 Hz, 1H, ArH), 6.95 (s, 1H, ArH), 6.96 (d, J 8.6 Hz, 1H, ArH).

Example 6.2

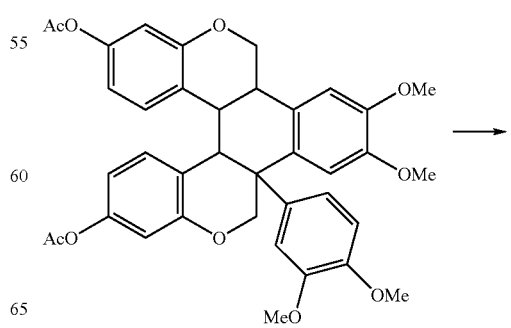

-continued

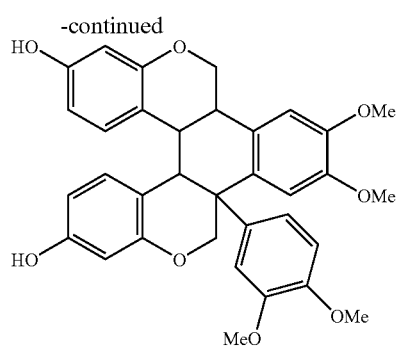

Imidazole (550 mg) was added to a suspension of 4,9-diacetoxy-14,15-dimethoxy-12a-(3',4'-dimethoxyphenyl)-2,11-dioxa-(1H,12H)-6b,6c,12a,16b-tetrahydronaphtho[1,2-g]chrysene (230 mg) in absolute ethanol (8 ml) and the mixture was refluxed for 45 min under argon. The solution was concentrated under reduced pressure and the product was precipitated by addition of distilled water (10 ml). The mixture was left overnight in the fridge and filtered to yield 4,9-dihydroxy-14,15-dimethoxy-12a-(3',4'-dimethoxyphenyl)-2,11-dioxa-(1H,12H)-6b,6c,12a,16b-tetrahydronaphtho[1,2-g]chrysene (1) as a white solid (100 mg, 50%).

$^1$H NMR (CDCl$_3$): δ 3.03 (dt, J 3.4 Hz, J 11.3 Hz, 1H, CH), 3.28 (d, J 12.4 Hz, 1H, CH), 3.75, 3.84, 3.85, 3.86 (each s, 3H, OCH$_3$), 3.92 (d, J 10.5 Hz, 114, CHa), 4.16 (s, 1H, CH), 4.56 (d, J 11.3 Hz, CHa'), 4.68 (d, J 11.3 Hz, CHb'), 4.77 (dd, J 3.7 Hz, J 10.5 Hz, 1H, CHb), 6.13 (dd, 1H, J 2.6 Hz, J 8.3 Hz, 1H, ArH), 6.20 (d, J 2.3 Hz, 1H, ArH), 6.36 (d, J 2.3 Hz, 1H, ArH), 6.45 (dd, J 2.6 Hz, J 8.3 Hz, 1H, ArH), 6.62-6.67 (m, 2H, ArH), 6.72 (d, J 8.3 Hz, 1H, ArH), 6.78 (d, J 8.3 Hz, 1H, ArH), 6.93 (s, 1H, ArH), 7.09 (d, J 9.0 Hz, 1H, ArH), 7.11 (s, 1H, OH), 7.70 (s, 1H, OH). $^{13}$C NMR (CDCl$_3$): δ 33.7 (CH), 36.2 (CH), 41.7 (CH), 47.2 (aliphatic C), 55.0, 55.1, 55.3, 55.5 (OCH$_3$), 69.4 (CH$_2$), 72.1 (CH$_2$), 102.9 (CH), 103.2 (CH), 107.8 (CH), 108.2 (CH), 109.0 (CH), 111.4 (CH), 112.0 (CH), 113.4 (CH), 114.4, 116.0 (ArC), 120.8 (CH), 126.8 (CH), 128.8 (CH), 129.1, 129.4, 139.0, 148.1, 148.3, 148.5, 149.3, 155.6, 156.4, 156.6, 156.9 (ArC). $\lambda_{max}$ 285 mm (ε 13,028), 217 37,743). $\nu_{max}$ 3322, 2933, 1618, 1516, 1463, 1255, 1166, 1024, 834, 742 cm$^{-1}$. Found: (HRESMS) m/z 591.196772; C$_{34}$H$_{32}$O$_8$Na requires m/z 591.198918.

The related analogous dimeric compounds were prepared by the above methods utilising correspondingly substituted readily obtainable starting materials.

1. Anticancer Activity

Dehydroequol (3-(4-hydroxyphenyl)chrom-3-en-7-ol) elicits cytotoxic effects against a broad range of human cancer cell lines and recent reports have shown that Phenoxodiol is a strong topoisomerase II inhibitor, a cell cycle disrupter, inhibits sphingosine kinase activation and down-regulates transcription of angiogenic matrix metalloprotease 2 and can induce apoptosis in chemoresistant ovarian cancer cells by regulating anti-apoptotic machinery.

Cisplatin anti-cancer activity has been observed in testicular tumors, ovarian carcinoma, bladder tumors, head and neck, breast cancer, lung cancer, refractory non-Hodgkins lymphomas. Cisplatin is a square planar, coordination complex (cis-diamminedichloroplatinum) thought to enter the cell either via a transmembrane channels or high capacity facilitated transport. Once cisplatin enters the cell, the chloride concentration drops to 20 µM and the drug undergoes strong hydration to form positively charged active species for subsequent interaction with cellular nucleophiles such as DNA and protein. Cisplatin reacts with nuclear DNA to yield a variety of adducts that include interstrand and intrastrand DNA cross-links and DNA-protein cross-links. The most common adduct is an intrastrand cross-link between adjacent guanines. Although genomic DNA is generally accepted as the critical pharmacological target of cisplatin-induced cytotoxicity, there is evidence that other cellular components that are damaged by cisplatin (RNA, proteins, membrane phospholipids, cytoskeletal microfilaments, and thiol-containing molecules) facilitates cisplatin induced cytotoxicity. Cisplatin-DNA adducts (DNA damage) are then detected by p53 which in turn initiates proapoptotic cascade probably via Bax/Bcl-2 modulation and typically induces a GI arrest. Necrosis has also been demonstrated as a mode of cisplatin cell death. Cisplatin has numerous adverse effects including intractable, almost universal, nausea and vomiting, anaphylactic-like reactions, neurotoxicity, myelosuppression, thrombocytopenia, granulocytopenia and dose limiting nephrotoxicity which is cumulative and irreversible.

Biological Studies and Screening Data

Screening studies have identified 4,9-dihydroxy-14,15-dimethoxy-12a-(3',4'-dimethoxyphenyl)-3,10-dimethyl-2,11-dioxa-(1H,12H)-6b,6c,12a,16b-tetrahydronaphtho[1,2-g]chrysene (2) as having a favourable in vitro toxicity profile against normal cells, and broad activity, comparable with and in some cases better than dehydroequol or cisplatin, against cancer cells representative of leukaemic, glioma, prostate, ovarian, breast, colorectal and lung cancer.

Materials and Methods—Tissue Cultures

Neonatal foreskin fibroblasts (NFF) were a gift from Dr. Peter Parsons (Queensland Institute of Medical Research). RK-13 (rabbit kidney) cells were obtained from Miller Whalley (Macquarie University). Both cell types were cultured in RPMI supplemented with 10% FCS (CSL, Australia), penicillin (100 U/ml), streptomycin (100 mg/ml), L-glutamine (2 mM) and sodium bicarbonate (1.2 g/L), and cultured at 37° C. in a humidified atmosphere of 5% CO$_2$.

The human pancreatic cancer cell line, HPAC (CRL-2119) was routinely cultured in 1:1 mixture DMEM (Sigma) plus Ham's F12 (Sigma) medium containing HEPES (15 mM), insulin (0.002 mg/ml), transferrin (0.005 mg/ml), hydrocortisone, (40 ng/ml), epidermal growth factor (10 ng/ml). The ovarian cancer cell line CP70 was obtained as a gift from Dr. Gil Mor (Yale University) and cultured in a 1:1 mixture DMEM plus Ham's F12 medium, and SKOV-3 was purchased from ATCC and cultured in McCoy's 5a medium. The breast cancer cell line MDA-MB-468 cultured in Leibovitz's L-15 medium.

All cultures were supplemented with 10% FCS(CSL, Australia), penicillin (100 U/ml), streptomycin (100 mg/ml), L-glutamine (2 mM) and sodium bicarbonate (1.2 g/L), and cultured at 37° C. in a humidified atmosphere of 5% CO$_2$. All remaining cell lines were purchased from ATCC (Maryland, USA) except where noted.

Proliferation Assays

IC50 values were determined for each cell line. Cells were seeded in 96-well plates at an appropriate cell density as determined from growth kinetics analysis. NFFs were cultured for 5 days and RK-13s for 24 hrs in the absence and presence of the test compounds. Cell proliferation was assessed after the addition of 20 µl of 3-4,5 dimethylthiazol-2,5-diphenyl tetrazolium bromide (MTT, 2.5 mg/ml in PBS, Sigma) for 3-4 hrs at 37° C. according to manufacturer's instructions. IC50 values were calculated from semi-log plots of % of control proliferation on the y-axis against log dose on the x-axis.

Example 7

Normal Cell Toxicity

Duplicate cytotoxicity assays against NFF cells were conducted with dehydroequol (DHE), 4,9-dihydroxy-14,15-dimethoxy-12a-(3',4'-dimethoxyphenyl)-3,10-dimethyl-2,11-dioxa-(1H,12H)-6b,6c,12a,16b-tetrahydronaphtho[1,2-g]chrysene (2) from Example 6.1 and cisplatin.

TABLE 2

Relative toxicity of dehydroequol, Cpd. 2 and cisplatin against neonatal foreskin fibroblasts (NFF) and rabbit kidney cells.

| | | Analogue (IC50 μM) | | Antineoplastic (IC50 μM) |
|---|---|---|---|---|
| Tissue/cell type | Designation | DHE | Cpd. 2 | Cisplatin |
| Fibroblast | NFF | >150 | 23.6 ± 6.6 | 9.85 ± 5 |
| Kidney | Rabbit Kidney | >150 | 36.0 ± 2.7 | NT |

Dimer 2 was found to be less toxic to normal cells than cisplatin, but more toxic than dehydroequol.

Example 8

Pharmacokinetics of Cpd. 2—Oral 4,9-Dihydroxy-14,15-dimethoxy-12a-(3',4'-dimethoxyphenyl)-3,10-dimethyl-2,11-dioxa-(1H,12H)-6b,6c,12a,16b-tetrahydronaphtho[1,2-g]chrysene (2) from Example 6.1 was prepared as homogenous suspensions in 1% CMC (m:v, water). The Cpd. 2 formulation was delivered orally by gavage to female BALB/c mice at a dosage of 50 mg/kg. Three animals were allocated to each time point (15 min, 30 min, 1 hr, 4 hr and 24 hr). At each respective time point, animals were euthanased by cervical dislocation and blood collected. Free Cpd. 2 was analysed by mass spectroscopy and the results are shown in Table 3.

TABLE 3

Comparative oral pharmacokinetic data for dehydroequol and Cpd. 2.

| | DHE (μM) | | Cpd. 2 (μM) | |
|---|---|---|---|---|
| Time | Free | Total | Free | Total |
| 0.25 | 3.3 | 511.5 | 1.332 | 1.393 |
| 0.5 | 2.9 | 357 | 4.930 | 6.453 |
| 1 | 1.5 | 387 | 6.756 | 10.778 |
| 4 | 1.3 | 117.6 | 6.314 | 7.634 |
| 24 | 0.15 | 0.13 | 1.148 | 1.704 |
| Dose* | 4.6 mg/ml | | 8.3 mg/ml | |

Dimer 2 was found to have a superior half-life at times up to 4 hours compared to dehydroequol. Dimer 2 was found to have a slow rate of conjugation compared to dehydroequol. The in vivo toxicity data showed that mice receiving 50 mg/kg 5063 (i.p.) over 9 consecutive days was not toxic as determined by weight loss and vital organ histology.

Example 9

In Vitro Cytotoxicity of Cpd. 2 as Monotherapy Against Cancer Cells

Dimer 2 demonstrated from comparable to markedly superior activity against a variety of malignant and multi-drug resistant cell lines when compared to dehydroequol or cisplatin IC50 values as shown in Table 4.

TABLE 4

Comparison of Dehydroequol, Cpd. 2 and cisplatin cytoxicity against cell lines representative of different malignancies

| | | Analogue (IC50 μM) | | Antineoplastic (IC50 μM) |
|---|---|---|---|---|
| Indication | Designation | DHE | Cpd. 2 | Cisplatin |
| Ovarian | A2780 | 1.7 ± 0.61 | 10.16 ± 0.07 | 2.10 |
| | CP70 | 1.69 ± 0.62 | 8.23 ± 3.73 | 10.30 |
| | SKOV-3 | 21.83 ± 4.65 | 16.7 ± 10.03 | 5.40 |
| Prostate | PC3 | 9.09 ± 8.12 | 7.36 ± 1.35 | 2.11 |
| | LNCaP | 4.8 ± 3.8 | 11.97 ± 4.3 | >10 |
| | DU145 | 5.95 ± 1.5 | 8.84 ± 0.47 | 2.07 |
| Breast | MCF-7 | 21.5 ± 13.2 | 10.28 | 3.69 |
| | MDA-MB-468 | 7.9 ± 3.5 | 8.59 ± 0.35 | 0.58 |
| Glioma | HTB-138 | 7.35 ± 0.89 | 16.37 | 42.30 |
| Pancreatic | CRL-2119 | 56.62 ± 16.8 | 11.23 ± 4.7 | 9.36 |
| Leukemic | RPMI-8226 | 3.72 ± 0.08 | 15.16 | NT |
| | CCRF-CEM | 1.7 ± 0.68 | 10.31 ± 1.33 | NT |
| Lung | NCI-H23 | 8.75 ± 7.2 | 16.37 | NT |
| | NCI-H460 | 10.6 ± 3.8 | 11.26 ± 4.97 | 22.29 |
| Colorectal | HT-29 | 50.45 ± 21.9 | 11.45 ± 6 | 22.7 ± 35 |
| | HCT-15 | 24.4 ± 12.57 | 54.67 ± 28 | 129.9 ± 39 |
| Melanoma | MM200 | 4.8 | 6.5 | 8.82 |
| | MM96L | 4.7 | 6.8 | 4.6 |

2. Anti-inflammatory Activity

Prostaglandins eg $PGE_2$ and $PGI_2$ and thromboxanes (TXs) eg $TXA_2$ are members of a family of fatty acid derivatives known as eicosanoids (Penglis et al. 2000). They are involved in both normal physiology and inflammatory responses, but have opposing effects on eg cytokine release and platelet aggregation. Release of arachidonic acid (AA) from membrane phospholipids provides the primary substrate for eicosanoid synthesis. Action of the cyclooxygenase (COX) enzymes, regardless of isotype, causes synthesis of the intermediate prostaglandin $PGH_2$, the common precursor for $PGE_2$, $PGI_2$ and $TXA_2$. Prostanoids play an important modulatory role in the immune response through complex interactions with leukocytes and parenchymal cells in the inflamed organ. They can produce both pro- and anti-inflammatory actions depending upon the inflammatory stimulus, the predominant prostanoid produced, and the profile of prostanoid receptor expression (Tilley et al. 2001).

Inhibition of TX synthase leads to reduced formation of TXs, and because there is an increased availability of the substrate $PGH_2$ for PG synthase, an increase in synthesis of PGs, (Carty et al. 2000; Penglis et al. 2000). An increase in $PGE_2$ can exert anti-inflammatory effects. For example:

a. $PGE_2$ has been reported to attenuate some acute inflammatory responses, in particular those initiated by mast cell degranulation (Raud et al. 1988).

b. $PGE_2$ suppresses, whereas $TXA_2$ increases $TNF_\alpha$ and IL-1β (Caughey et al. 1997). Inhibition of $TXA_2$ is a potential way of inhibiting inflammatory cytokine production, particularly that of TNF. Currently, biological therapies which suppress TNF levels (with antibodies or soluble TNF receptor shave been successful in treating rheumatoid arthritis which is refractory to, or no longer responsive to other therapies. A chemical agent which suppressed TNF production and which could be taken orally would be a great advance. Inhibition of $TXA_2$ formation may be a means of suppressing production of TNF, a cytokine which is involved in the signs and symptoms of joint inflammation and in the longer term degradative phase of joint inflammation manifest in cartilage degradation, diminution of joint space and ultimately, joint failure.

c. $PGE_2$ inhibits a wide range of T and B cell functions including inhibition of T lymphocyte activation and proliferation and Ig production (Tilley et al. 2001). Conversely, $TXA_2$ may promote T cell activation and proliferation and facilitate the development of effector cytolytic T cells (CTLs). Altering this balance in favour of PG production may facilitate 'quenching' of an inappropriate immune response as occurs in autoimmune disease.

d. In asthma, $PGE_2$ promotes vasodilation and increases vascular permeability (Tilley et al. 2001). As inflammation progresses, $PGE_2$ synthesis by macrophages is enhanced due to increased expression of COX-2 and PGE-synthase. $PGE_2$ inhibits leukocyte activation and promotes bronchodilation. $TXA_2$ synthase inhibitors and thromboxane prostanoid (TP) receptor antagonists have been developed as anti-asthma drugs (Shi et al. 1998).

e. In glomerulonephritis there is co-activation of the AA COX pathway toward synthesis of PGs and TX and of lipoxygenase pathways toward synthesis of leukotrienes. $TXA_2$ is the most abundant eicosanoid synthesized in nephritic glomeruli, and $TXA_2$ synthase inhibitors (eg Dazmegrel) are now available for the treatment of glomerulonephritis. In a rat model of nephritis, Dazmegrel increased $PGE_2$ synthesis which is useful as $PGE_2$ preserves kidney function in glomerulonephritis (Lianos et al. 1999).

f. Thromboxanes may play a major pathogenic role in inflammatory bowel disease (IBD). TXs are produced in excess not only in inflamed mucosa but also in Crohn's disease by uninflammed bowel and by isolated intestinal and peripheral blood mononuclear cells. Their cellular source is likely to include platelets, neutrophils, endothelial and epithelial cells as well as mononuclear cells (Rampton et al. 1993; McCartney et al. 1999; Carty et al. 2000; Carty et al. 2002). The pro-inflammatory effects of TXs are both direct (diapedesis and activation of neutrophils, mucosal ulceration, reduction of suppressor T-cell activity) and indirect (vasoconstriction, platelet activation) (Rampton et al. 1993). PGs are thought to be protective to gastrointestinal mucosa (Carty et al. 2000). Sulfasalazine, a compound frequently administered in the treatment of chronic IBD, as well as one of its main metabolites, sulfapyridine, have been demonstrated to inhibit synthesis of $TXB_2$ while enhancing synthesis of $PGF_2$, or $PGE_2$, respectively (Hawkey et al. 1985). In other words, they would appear to have some level of TX synthase inhibition.

Materials and Methods—Tissue Cultures

Human peripheral blood monocytes (from three separate individuals) were isolated from buffy coats by lymphoprep gradient separation of mononuclear cells followed by counter-current centrifugal elutriation (Demasi et al. 2000). The test compounds were dissolved in DMSO and added to fresh monocytes After 30 min, LPS was added to achieve a final concentration of 200 ng/mL. After incubation for 18 hrs at 37° C. in 5% $CO_2$, supernatants were removed and $PGE_2$, $TXB_2$ (the stable hydrolysis product of $TXA_2$) and TNFα production were measured by radioimmunoassay (RIA).

The mouse macrophage cell line RAW 264.7 was cultured in DMEM supplemented with FCS, 2 mM glutamine and 50 U/ml penicillin/streptomycin. Subconfluent cells were detached from the flask by gentle scraping and 24-well plates seeded at $5 \times 10^5$ cells per well and allowed to adhere for 1 hr. Cells were then treated either test compounds (in 0.025% DMSO) or vehicle alone, and incubated for 1 hr. LPS 50 ng/ml (LPS —Sigma-Aldrich) was then added. After incubation for 16 hrs, culture media was collected and stored at −80° C. for ecosanoid and cytokine measurements using enzyme immunometric assays ($PGE_2$ and $TXB_2$—Cayman Chemical and TNFα—Becton Dickinson).

Results and Conclusions

FIGS. 1 to 8 show that both dimers, Cpd. 1 and Cpd. 2, inhibited $TXB_2$ and induced $PGE_2$ in a dose responsive manner in murine macrophages (RAW 264.7) and human monocytes stimulated with LPS. As well, Cpd. 1 and Cpd. 2 inhibited the induction of TNFα in human monocytes. The dimeric compounds of the invention are useful in the treatment of inflammatory diseases and related conditions.

3. Cardiovascular Activity

Materials and Methods

Male Sprague-Dawley rats (250±50 g) were euthanased with 80% $CO_2$ and 20% $O_2$. The thoracic aorta was excised and quickly mounted in organ-baths as described (Chin-Dusting et al, 2001). Full concentration-contractile curves were obtained to noradrenaline (0.1 mM-10 mM) in the absence and presence of Cpd. 2 (1 μg/ml). Experiments were repeated in n=6 different rings from 6 different animals.

Figure 9:
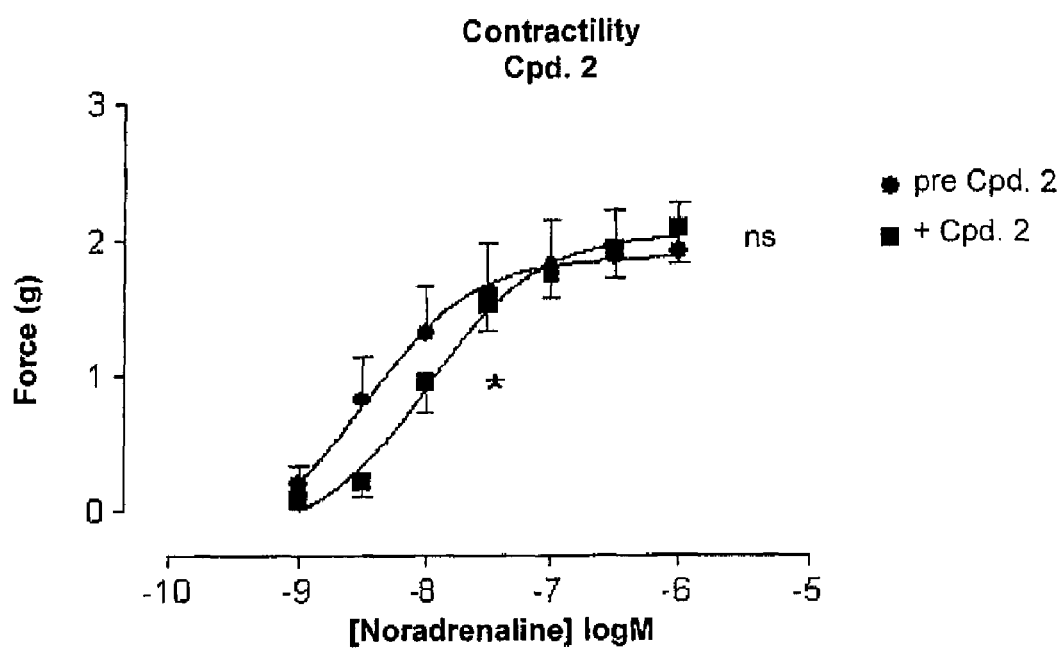
FIG. 9 shows the effect of Cpd. 2 on the aortic contractility induced by noradrenaline.
Figure 9:
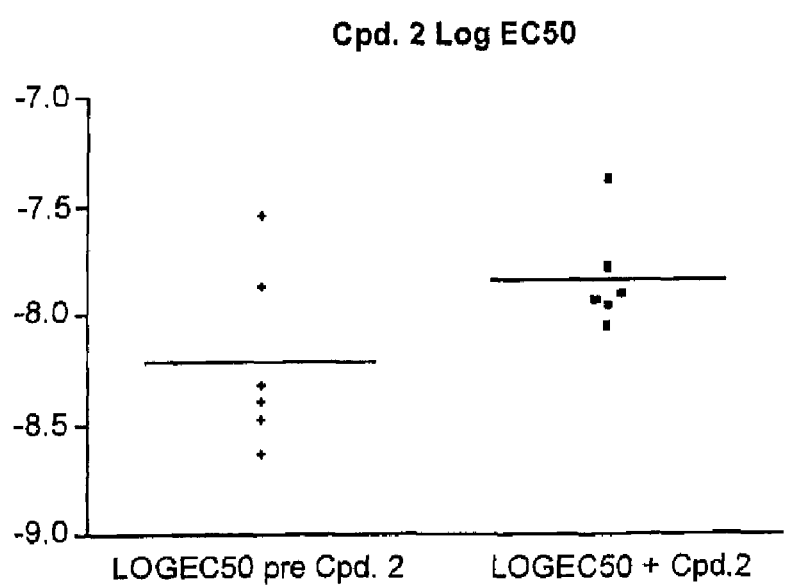

Cpd. 2 had no effect on maximal contractile response to noradrenaline (1.94±0.35 vs. 2.09±0.23; p>0.05) but significantly shifted the neg log $EC_{50}$ concentration of noradrenaline from −8.21±0.17 to −7.84±0.097 (p<0.05) showing that Cpd. 2 was able to antagonise (or block) the contractile effect of noradrenaline (see FIG. 9).

Results and Conclusions

Cpd. 2 has demonstrated activity against aortic ring contractility induced by noradrenaline. These data indicate that Cpd. 2 exhibits vasodilatory activity and inhibits vasoconstriction.

4. Chemosensitisation

The utility of the dimeric compounds of the invention to act as a chemosensitiser when used in combination with an array of standard chemotherapeutic agents was assessed. Dimeric Cpd. 2 was applied to various colorectal and pancreatic cancer cell lines to investigate its synergy with standard chemotherapeutic agents including cisplatin, gemcitabine, paclitaxel, doxorubicin, camptothecin and topotecan.

Experimental Design

The experiment as outlined in SOP-BD011 (Versions A and B) was used to screen three antineoplastic agents against a given cell line in any 'one' experiment (see for example Kanzawa et al., (1997)). The inherent design of the experiment allowed for three sequences of Cpd. 2 and an antineoplastic agent.

1) Direct Sequence—Cells are treated with both Cpd. 2 and a single antineoplastic agent (combined) for 5 days.
2) Cpd. 2 First (Forward) Sequence—Cells are treated for 24 hours with Cpd. 2 before replacing with a 24 hour antineoplastic agent treatment; drugs are then washed out and processed on Day 5.
3) Reverse Sequence—The reverse order to experiment No. 2 above. i.e. a cytotoxin first sequence Results and Conclusions All data was evaluated using the formulae of theoretic additivity incorporated into a three dimensional model, as described by Kanzawa et al. (1997). This allows for simple data interpretation as values in excess of 10% are defined as 'synergistic' (depicted in grey) whilst those below −10% are defined as 'antagonistic' (depicted in black).

Figure 10:
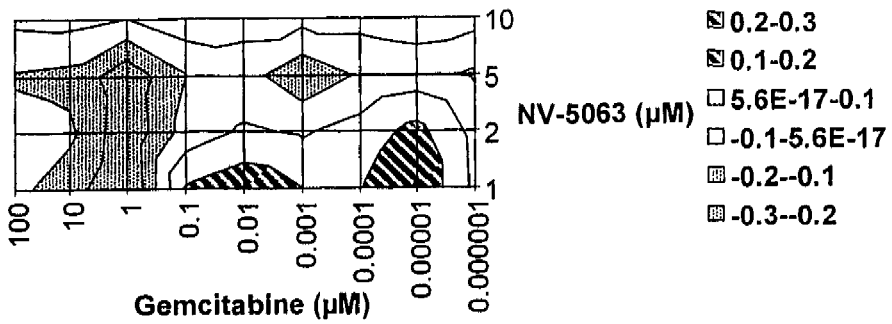
FIG. 10 shows the synergistic effect of Cpd. 2 and Gemcitabine on HPAC (Pancreatic) cells. Plot A depicts the combination of Cpd. 2 and Gemcitabine, whilst B and C are 24 hour forward (Cpd. 2 first) and reverse (Gemcitabine first) sequences respectively.
Figure 10:
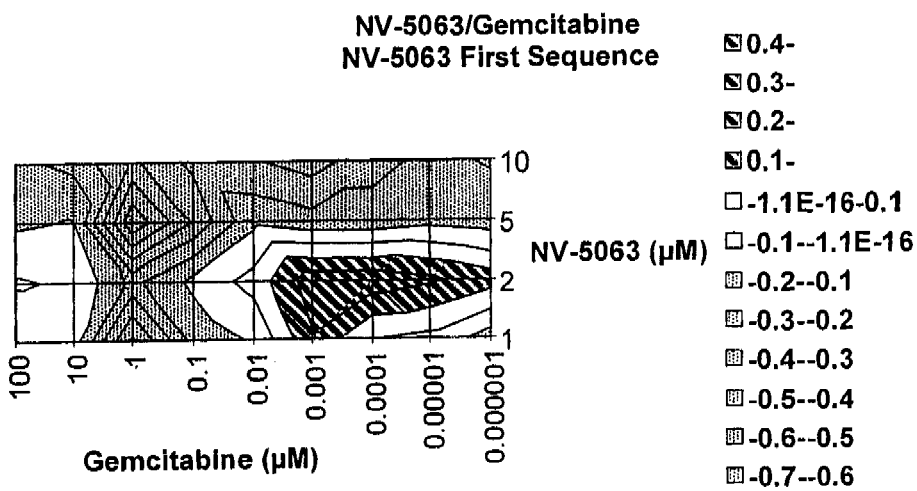
Figure 10:
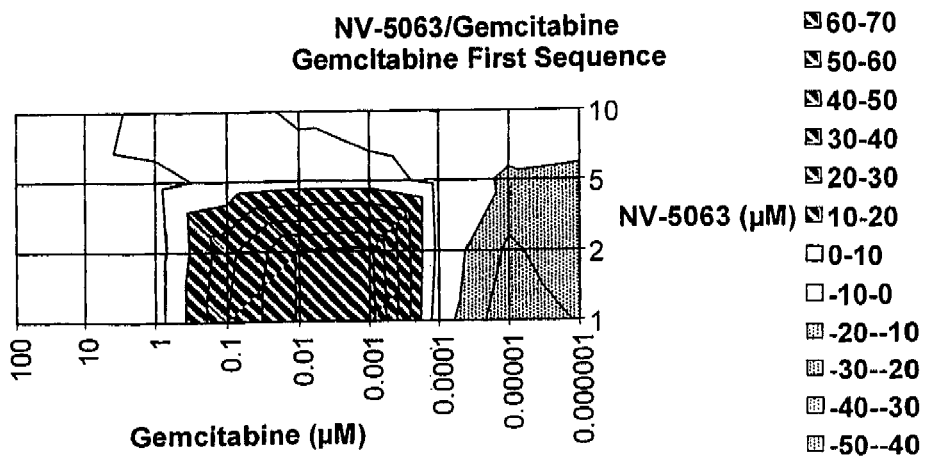

The combination of Cpd. 2 and Gemcitabine resulted in synergistic cytotoxicity to HPAC cells when treated simultaneously (A) or over 24 hour sequences (B,C) (see FIG. 10). This effect was apparent over a larger concentration range in both of the 24 hour sequence data. Synergy was not observed at Cpd. 2 concentrations greater than 5 µM.

Figure 11:
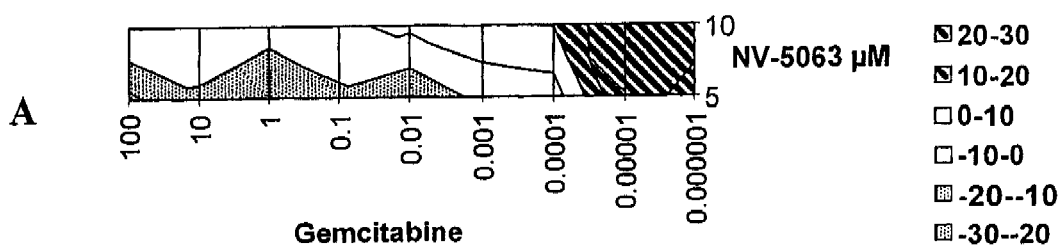
FIG. 11 shows HT-29 (Colorectal) cells treated sequentially with Cpd. 2 (at 5 μM and 10 μM) and nine serially diluted Gemcitabine concentrations in both the forward (A) and reverse (B) sequences.
Figure 11:
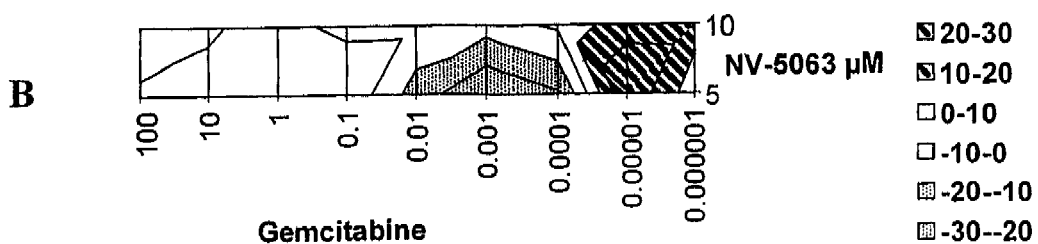

The combination of Cpd. 2 and Gemcitabine resulted in synergistic cytotoxicity to HT-29 cells in both the forward (A) and reverse (B) sequences (see FIG. 11).

Figure 12:
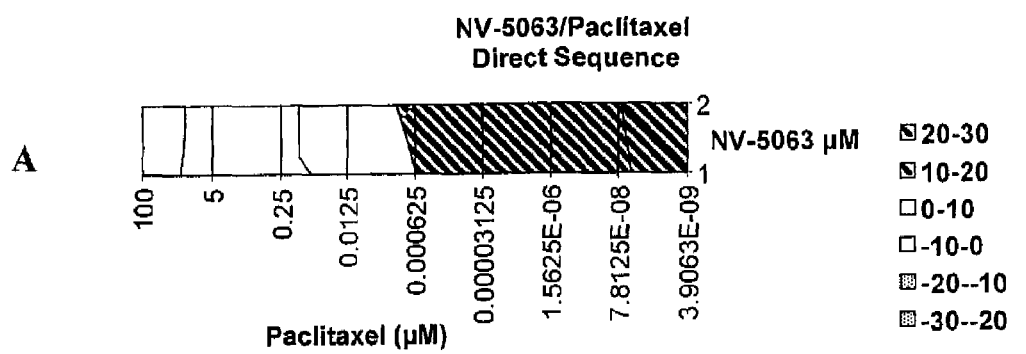
FIG. 12 shows the synergistic effect of Cpd. 2 (at 1 μM and 2 μM) and Paclitaxel on HT-29 (Colorectal) cells. Plot A depicts the combination of Cpd. 2 and Paclitaxel, whilst B and C are 24 hour forward (Cpd. 2 first) and reverse (Paclitaxel first) sequences respectively.
Figure 12:
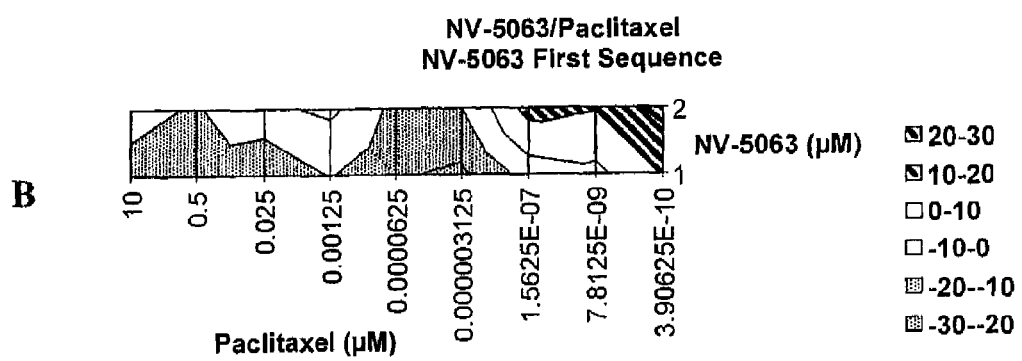
Figure 12:
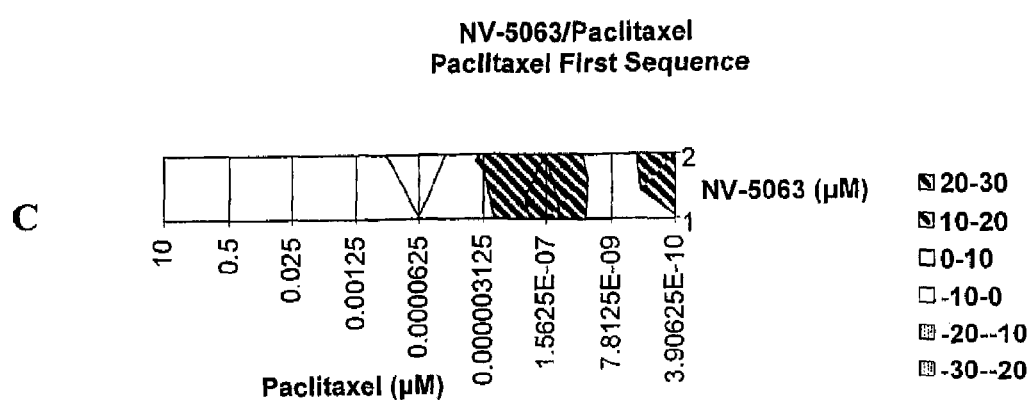

HT-29 cells treated with Cpd. 2 (at 1 µM and 2 µM) and nine serially diluted Paclitaxel concentrations demonstrate strong synergy when treated in combination (A) (see FIG. 12). Less significant regions of synergy are also seen in both the forward (B) and reverse (C) 24 hour sequences.

Figure 13:
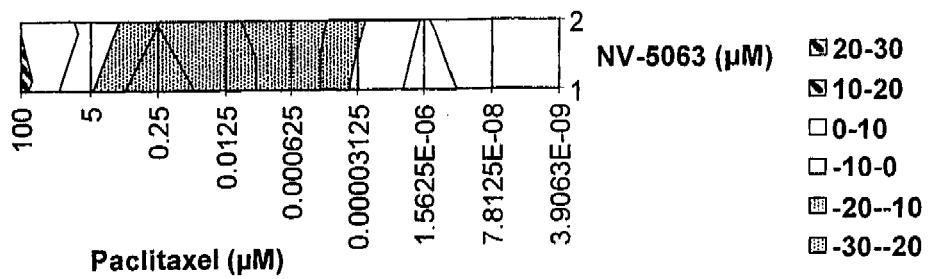
FIG. 13 shows the synergistic effect of Cpd. 2 (at 1 μM and 2 μM) and Paclitaxel on HCT-15 (Colorectal) cells. Plot A depicts the combination of Cpd. 2 and Paclitaxel, whilst B and C are 24 hour forward (Cpd. 2 first) and reverse (Paclitaxel first) sequences respectively.
Figure 13:
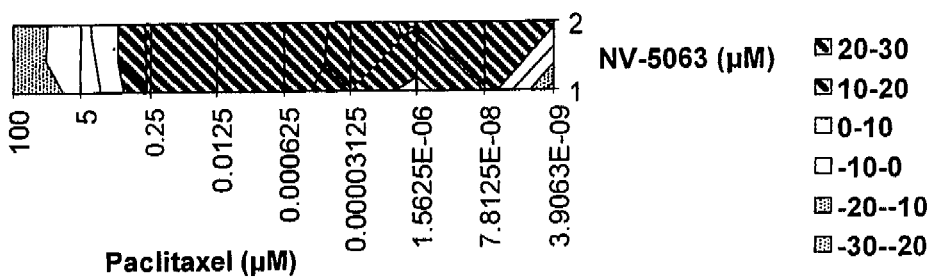
Figure 13:
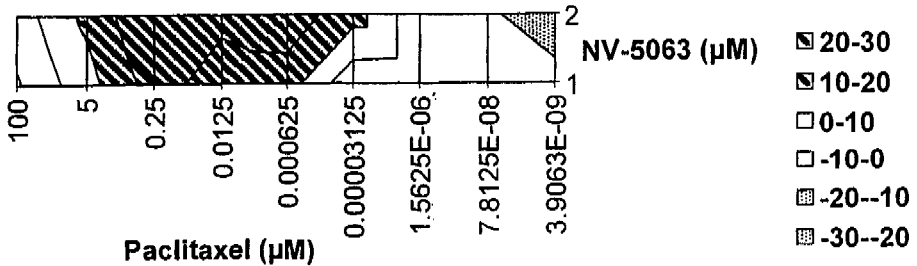

HCT-15 cells treated with Cpd. 2 (at 1 µM and 2 µM) and nine serially diluted Paclitaxel concentrations demonstrate strong synergy when sequentially treated in both the forward (B) and reverse (C) 24 hour sequences (see FIG. 13). For comparison, no synergy is observed in the combination treated group (A).

Figure 14:
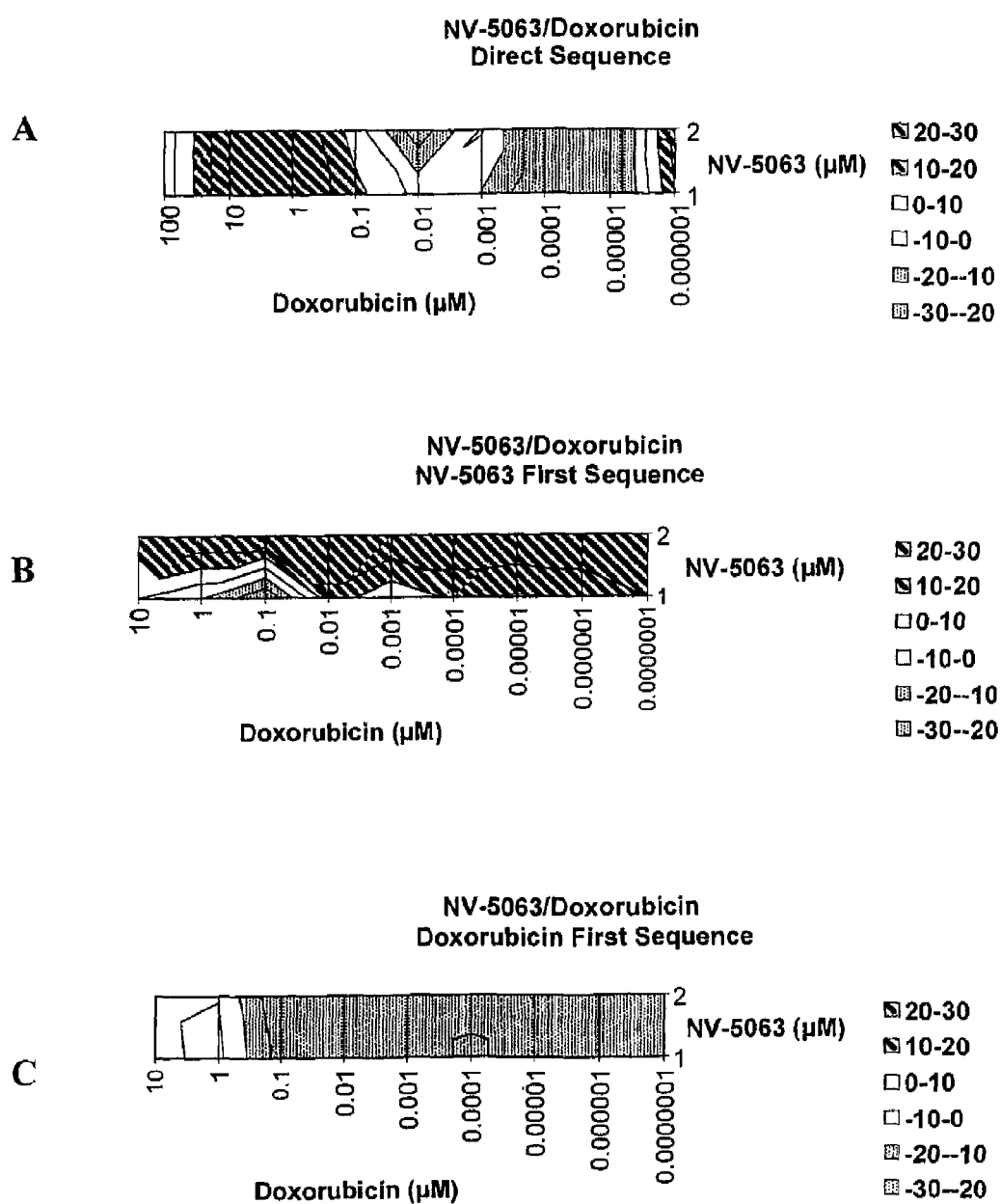
FIG. 14 shows the synergistic effect of Cpd. 2 (at 1 μM and 2 μM) and Doxirubicin on HT-29 (Colorectal) cells. Plot A depicts the combination of Cpd. 2 and Doxirubicin, whilst B and C are 24 hour forward (Cpd. 2 first) and reverse (Doxirubicin first) sequences respectively.

The combination of Cpd. 2 and Doxorubicin resulted in strong synergistic cytotoxicity to HT-29 cells when treated in both combination (A) and forward (B) sequences (see FIG. 14). When the cells were treated with Doxorubicin first, no synergy was observed (C).

Figure 15:
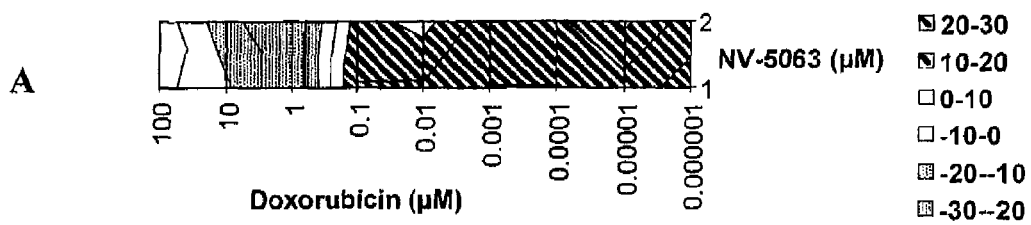
FIG. 15 shows the synergistic effect of Cpd. 2 (at 1 μM and 2 μM) and Doxirubicin on HCT-15 (Colorectal) cells. Plot A depicts the combination of Cpd. 2 and Doxirubicin, whilst B and C are 24 hour forward (Cpd. 2 first) and reverse (Doxirubicin first) sequences respectively.
Figure 15:
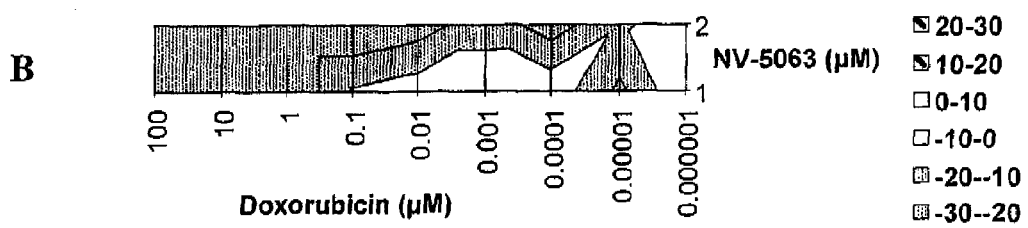
Figure 15:
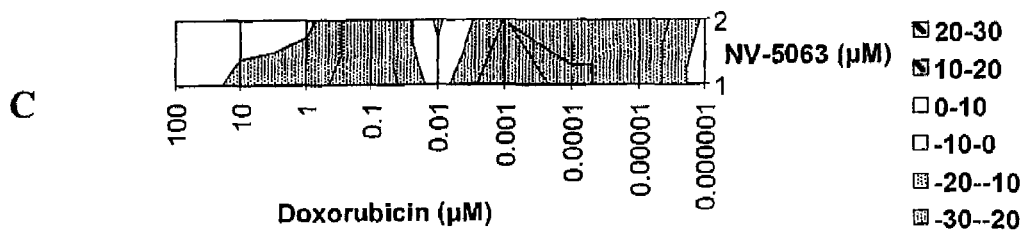

The combination of Cpd. 2 and Doxorubicin resulted in strong synergistic cytotoxicity to HCT-15 cells when treated in combination (A) (see FIG. 15). No synergy was observed in either the forward (B) or reverse (C) sequences.

Synergy was routinely seen between Cpd. 2 and the chemotherapy drugs, Gemcitabine, Paclitaxel and Doxorubicin. The data suggests that Cpd. 2 can synergise with these agents optimally when Cpd. 2 is administered in a 24 hour sequence, in either forward or reverse direction. The results show that the dimeric compounds of the invention are particularly efficacious in the chemosensitisation of tumour cells and the chemo-protection of non-tumour cells.

5. Anti-Inflammatory Activity in Murine Ear Inflammation

Compound 2 was examined for its ability to inhibit ear swelling in mice induced by the topical application of arachidonic acid (AA). The inflammatory response due AA, the immediate precursor of the eicosanoids, is due to formation of AA metabolites via both the cyclooxygenase (COX) and lipoxygenase (LOX) pathways (Young et al. 1984). AA induces an early (10-15 min) increase in both $PGE_2$ and $LTC_4$ synthesis which precedes the increase in ear thickness (Opas et al. 1985; Chang et al. 1986).

Methods

Female BALB/c mice (ARC, WA, Australia), weighing 15-21 g were injected with Compound 2 delivered in polyethylene glycol (PEG) 400:phosphate buffered saline (PBS) 1:1 intraperitoneally (i/p) at a dose of 25 mg/kg 30 min prior to the application of AA being to the ears. Mice were anaesthetised using isoflurane and baseline thickness of both ears was measured using a spring micrometer. Each mouse received a total of 20 µL of AA in ethanol (50 mg/ml) applied to the inner and outer surfaces of each pinna (i.e. 0.5 mg AA or 2 µg PMA per ear). Mice were anaesthetised again to remeasure the ears at 1 hr post-AA application.

The difference in ear swelling pre- and post-application of AA for each ear was calculated, and the average for the two ears of each mouse calculated. The difference in mean swelling of each test group compared to the group given vehicle alone was calculated using a two-tailed unpaired t test (Prism 4, GraphPad Software).

Results

Treatment with Compound 2 resulted in a significant reduction in ear thickness compared with treatment with vehicle alone.

TABLE 1

Change in ear thickness in response to the application of AA

| Compound | Change in ear thickness (mean ± SD, ×0.01 mm) | difference between test group and vehicle |
|---|---|---|
| Vehicle | 14.5 ± 4.7 | — |
| Compound 2 | 5.1 ± 1.7 | p = 0.0018 |

This result demonstrates the anti-inflammatory activity of compound 2 in vivo.

6. Anti-Inflammatory Activity in Murine Model of the UV Irradiation-Induced Skin Oedema Acute exposure of mammalian skin to UV irradiation causes an inflammatory reaction manifested by erythema and oedema. This reaction is mediated in part by pro-inflammatory prostaglandins ($PGD_2$, $PGE_2$, $PGF_{2\alpha}$ and possibly $PGI_2$) and leucotrienes, as well as the generation of reactive free radicals and reactive oxygen species (Sondergaard et al. 1985; Gonzalez and Pathak 1996; Widyarini et al. 2001).

Methods

Groups of 4-5 female Skh:hr-1 albino mice were irradiated with 1×3 MEdD (minimal edematous dose) of solar simulated UV radiation (SSUV). Solar-simulated ultraviolet radiation (SSUV) was provided by a planar bank of 6 UVA tube (Hitachi 40W F40T 10/BL, black light) and one UVB tube (Philips TL 40W/12RS) with radiation filtered through a sheet of 0.125 mm cellulose acetate (Eastman Chemical Products, Kingport, Tenn., USA) to give 2.96×10-4W/cm2 UVA and 1.59×10-5W/cm2 UVB. The distance of the UV lamp from the irradiance table surface was approximately 20 cm and temperature was controlled with an electric fan. During irradiation, the cages were rotated below the lights to reduce the variation in radiation intensity in different positions.

Either test compound (0.2 ml of a 20 µM solution) or vehicle (propylene glycol/ethanol/water 1:2:1) was applied to the irradiated dorsal skin at 30 min, 2 h and 4 h post-irradiation. Dorsal skin fold measurements were made with a spring micrometer prior to and at 24 hr and 48 h post-UV exposure. The difference in skin thickness pre- and post-exposure to UVR was calculated for each mouse, and the differences examined between test compound and vehicle control were analysed using an unpaired two-tailed t test.

Results

Skin fold thickening was evident at 24 hrs post-UV irradiation and peaked at 48 hrs, the last time point measured. Even though test compounds were applied only three times post-UV irradiation, and dosing was completed 20 hrs prior to the first skin fold measurement, the compounds examined were active in reducing UV-induced inflammation, as highlighted in the tables and graphs below.

Compound 2 significantly inhibited skin oedema at both time points and Compound 1 significantly inhibited at 24 hrs

TABLE 2

The change in dorsal skin fold thickness at 24 hrs post-irradiation

| Compound | Change in skin thickness (mean ± SD, ×0.01 mm) | difference between test group and vehicle |
| --- | --- | --- |
| Vehicle | 78 ± 23 | — |
| Compound 1 | 51 ± 14 | p = 0.0284 |
| Compound 2 | 36 ± 22 | p = 0.003 |

TABLE 3

The change in dorsal skin fold thickness at 48 hrs post-irradiation

| Compound | Change in skin thickness (mean ± SD, ×0.01 mm) | difference between test group and vehicle |
| --- | --- | --- |
| Vehicle | 147 ± 37 | — |
| Compound 1 | 117 ± 20 | p = 0.1040 |
| Compound 2 | 105 ± 16 | p = 0.025 |

These results clearly demonstrate the anti-inflammatory activity of both Compound 1 and Compound 2. Even though they were administered topically and within a short interval after the induction of inflammation, their effects were still evident up to 48 hrs later.

7. Immunosuppressive Effect in Murine Splenocytes

Methods

Male Skh-1 (hairless) mice, six weeks old were killed by cervical dislocation. Single cell suspensions were made from their spleens and erythrocytes were lysed in buffer (0.14M $NH_4Cl$, 17 mM Tris, pH 7.2). The remaining splenocytes were cultured in RPMI-1640 (Gibco) supplemented with 10% (v:v) FBS, 200 mM L-glutamine, penicillin/streptomycin and 50 mM 2-mercaptoethanol. Splenocytes were added to triplicate wells containing either concanavalin A (ConA, Sigma-Aldrich—0.4 μg/well), lipopolysaccharide (LPS, Sigma-Aldrich—1 μg/well) or no mitogen, as well as 10 μM of either Compound 1 or Compound 2 in DMSO, or DMSO alone. Samples were analysed after a 3 day incubation at 37° C. in 5% $CO_2$ in air. To assess cell numbers, methylthiazoletetrazolium (MTT) was added to each well, incubated for a further 4 hrs and then colour developed with 0.04N HCl in isopropanol (Mosmann 1983). Plates were read at 570 nm and 630 nm. The compounds were examined several times using different mice. For each assay, the effect of test compound was compared with that of vehicle control, and the results compared using a student's t test (Prism). Statistically significant difference was determined to have occurred when $p<0.05$.

Another assay examined the effect pre-incubating unstimulated splenocytes with test compounds at 10 μM for 24 hours, removing the compounds and then assessing their ability to respond to mitogenic stimulation as described for the previous assay. Cell numbers were assessed after the 24 hr pre-incubation using MTT, and equal numbers of cells/well plated into 96 well plates as usual.

Results

Figure 16:
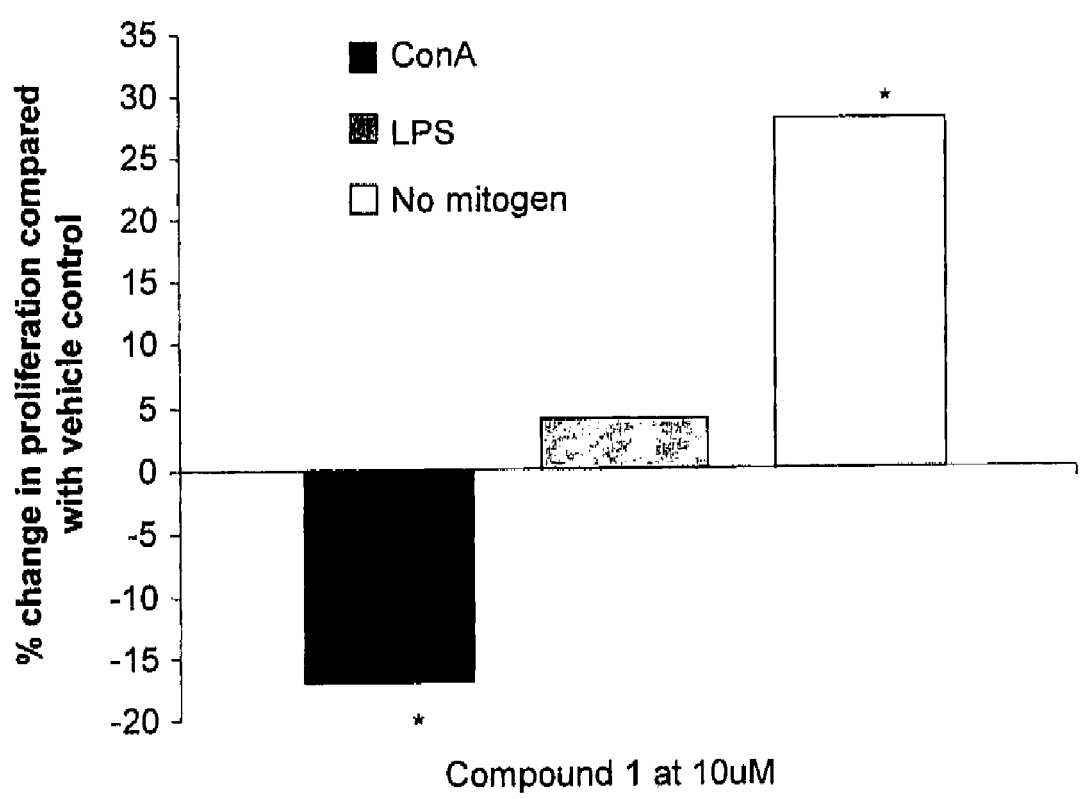
FIG. 16 shows the effect of Cpd. 1 (at 10 μM) on the inhibition of T cell proliferation.

The effect of incubation with 10 μM of Compound 1 was examined in six different assays. Compound 1 significantly inhibited T cell proliferation by 14-19% in 4/6 assays, but had no effect on B cell proliferation. Compound 1 significantly enhanced the proliferation of unstimulated splenocytes by 25-33% in 5/6 assays. The results from one representative assay are presented in FIG. 16.

Compound 2 at 10 μM was examined in four different assays. The results varied amongst assays, so that there was no consistent trend (data not shown).

At higher concentrations, both Compounds 1 and 2 reduced proliferation compared with vehicle control and regardless of the presence or absence of mitogenic stimulation (data not shown).

Figure 17:
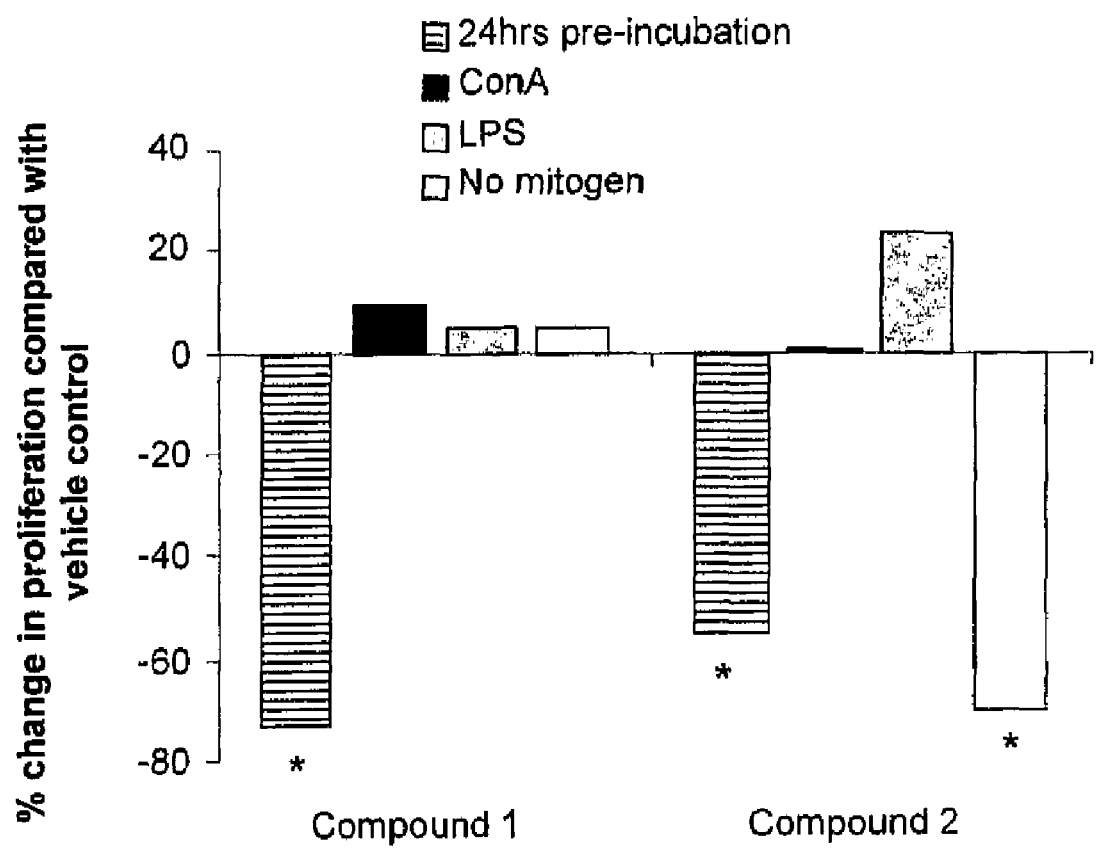
FIG. 17 shows the effect of Cpd. 1 and Cpd. 2 (both at 10 μM) on the inhibition of T cell proliferation following 24 hrs pre-incubation.

Following the pre-incubation with 10 μM of both Compounds 1 and 2 for 24 hrs, there was a marked and significant reduction in cell numbers compared with incubation with vehicle alone (Compound 1—73%; Compound 2—55%). Pre-incubation with Compound 1 had no effect on the response to ConA, whereas the proliferative response to ConA by cells pre-incubated with Compound 2 was significantly less than those pre-incubated with vehicle alone. Pre-incubation with neither compound affected the response to LPS. Splenocyte viability following three days' culture in the absence of mitogen, was not affected by Compound 1, but was significantly reduced by Compound 2 compared with those cells which had been pre-incubated with vehicle alone. The results are presented in FIG. 17.

These results suggest that both compounds may be cytotoxic to resting lymphocytes. Compound 1 does not appear to block resting lymphocytes in the $G_0$ or $G_1$ phase of the cell cycle, whereas Compound 2 may affect the cell cycle of resting T cells so that they are unable to respond to mitogenic stimulation, even in the absence of Compound 2.

The therapeutic implication is that these compounds have immunomodulatory activity, which contribute towards antinflammatory and cardiovascular activity in a variety of targets.

8. Toxicity Studies

Figure 18:
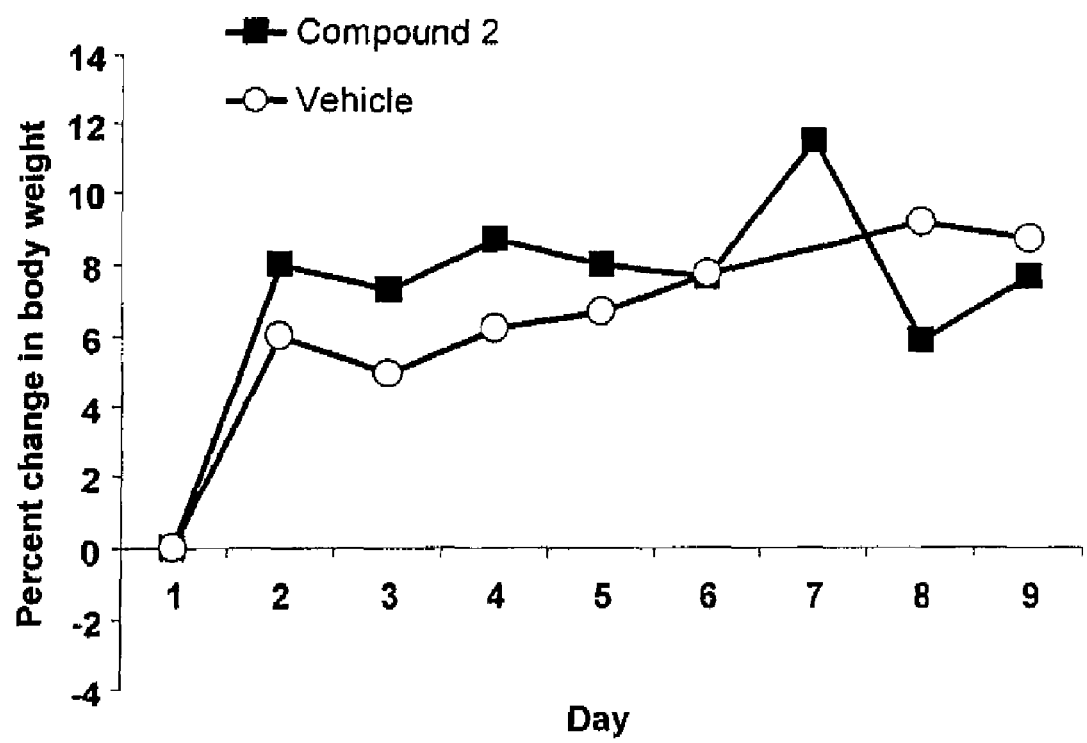
FIG. 18 shows a comparison of body weight change following i/p administration of either Cpd. 2 (at 50 mg/kg/day) or vehicle.

In a small study, BALB/cnu/nu mice were administered with either Compound 2 (n=2) as a solution in 6% Tween 20:PBS at 50 mg/kg or an equivalent volume of vehicle (n=2), by i/p injection. Mice were weighed and observed for signs of toxicity daily using clinical monitoring sheets. On day 9, mice were killed by cervical dislocation, and the kidney, spleen and liver of each mouse were collected for histological assessment of toxicity. See FIG. 18.

There was no difference in body weight gain, no abnormal clinical signs, in particular gastrointestinal side effects and no histological evidence of toxicity in any of the organs examined between mice given Compound 2 and those given vehicle alone Whilst not wishing to be bound by theory, the compounds of the present invention are thought to regulate a wide variety of signal transduction processes within animal cells and that these signal transduction processes are involved in a wide range of functions that are vital to the survival and function of all animal cells. Therefore, these compounds have broad-ranging and important health benefits in animals including humans, and in particular have the potential to prevent and treat important and common human diseases, disorders and functions, which represents a substantial unexpected benefit.

The particular benefits of this invention lie in (a) the large range of signal transduction processes targeted by the compounds, (b) the fact that regulation of these various processes includes both up-regulation of some processes and down-regulation of others, and (c) that such a broad and varied effect on signal transduction processes also is accompanied by an independent effect on a range of important enzymes that are fundamental to metabolism and steroidogenesis.

The reference to any prior art in this specification is not, and should not be taken as, an acknowledgment or any form of suggestion that that prior art forms part of the common general knowledge in the field of endeavour.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification individually or collectively, and any and all combinations of any two or more of said steps or features.

JOURNAL REFERENCES

Carty, E., M. Macey, S. A. McCartney and D. S. Rampton (2000). "Ridogrel, a dual thromboxane synthase inhibitor and receptor antagonist: anti-inflammatory profile in inflammatory bowel disease." Alimentary Pharmacology & Therapeutics 14(6): 807-17.

Carty, E., C. Nickols, R. M. Feakins and D. S. Rampton (2002). "Thromboxane synthase immunohistochemistry in inflammatory bowel disease." Journal of Clinical Pathology 55(5): 367-370.

Caughey, G. E., M. Pouliot, L. G. Cleland and M. J. James (1997). "Regulation of tumor necrosis factor-alpha and IL-1 beta synthesis by thromboxane A2 in nonadherent human monocytes." Journal of Immunology 158(1): 351-8.

Chang, J., et al. (1986). "Correlation between mouse skin inflammation induced by arachidonic acid and eicosanoid synthesis." Inflammation 10(3): 205-14.

Chin-Dusting, J. P., L. J. Fisher, et al. (2001). "The vascular activity of some isoflavone metabolites: implications for a cardioprotective role." British Journal of Pharmacology. 133(4): 595-605.

Demasi, M., G. E. Caughey, et al. (2000). "Assay of cyclooxygenase-1 and 2 in human monocytes." Inflammation Research 49(12): 737-43.

Gonzalez, S. and M. A. Pathak (1996). "Inhibition of ultraviolet-induced formation of reactive oxygen species, lipid peroxidation, erythema and skin photosensitization by polypodium leucotomos." Photodermatol Photoimmunol Photomed 12(2): 45-56.

Hawkey, C. J., N. K. Boughton-Smith and B. J. Whittle (1985). "Modulation of human colonic arachidonic acid metabolism by sulfasalazine." Digestive Diseases & Sciences 30(12): 1161-5.

Kanzawa, F., Nishio, N., Fukuoka, K., Fukuda, M., Kunimoto, T., and Saijo, N. (1997) "Evaluation of synergism by a novel three-dimensional model for the combined action of Cisplatin and Etoposide on the growth of a human small-cell lung-cancer cell line, SBC-3" International Journal of Cancer 71:311-9, 1997.

Lianos, E. A. and B. A. Bresnahan (1999). "Effect of thromboxane A2 inhibition and antagonism on prostaglandin and leukotriene synthesis in glomerular immune injury." Journal of Laboratory & Clinical Medicine 134(5): 478-82.

McCartney, S. A., J. A. Mitchell, P. D. Fairclough, M. J. Farthing and T. D. Warner (1999). "Selective COX-2 inhibitors and human inflammatory bowel disease." Alimentary Pharmacology & Therapeutics 13(8): 1115-7.

Mosmann, T. (1983). "Rapid colorimetric assay for cellular growth and survival: application to proliferation and cytotoxicity assays." Journal of Immunological Methods. 65(1-2): 55-63.

Opas, E. E., et al. (1985). "Prostaglandin and leukotriene synthesis in mouse ears inflamed by arachidonic acid." Journal of Investigative Dermatology 84(4): 253-6.

Penglis, P. S., L. G. Cleland, M. Demasi, G. E. Caughey and M. J. James (2000). "Differential regulation of prostaglandin E2 and thromboxane A2 production in human monocytes: implications for the use of cyclooxygenase inhibitors." Journal of Immunology 165(3):1605-11.

Rampton, D. S, and C. E. Collins (1993). "Review article: thromboxanes in inflammatory bowel disease—pathogenic and therapeutic implications." Alimentary Pharmacology & Therapeutics 7(4): 357-67.

Raud, J., S.-E. Dahlen, A. Sydbom, L. Lindbom and P. Hedqvist (1988). "Enhancement of acute allergic inflammation by indomethacin is reversed by prostaglandin E2: apparent correlation with in vivo modulation of mediator release." Proc. Natl. Acad. Sci. USA. 85: 2315-2319.

Shi, H., A. Yokoyama, N. Kohno, Y. Hirasawa, K. Kondo, K. Sakai and K. Hiwada (1998). "Effect of thromboxane A2 inhibitors on allergic pulmonary inflammation in mice." European Respiratory Journal 11(3): 624-9.

Sondergaard, J., et al. (1985). "Eicosanoids in skin UV inflammation." Photo-Dermatology 2(6): 359-66.

Tilley, S. L., T. M. Coffman and B. H. Koller (2001). "Mixed messages: modulation of inflammation and immune responses by prostaglandins and thromboxanes." Journal of Clinical Investigation 108(1): 15-23.

Widyarini, S., et al. (2001). "Isoflavonoid compounds from red clover (*Trifolium pratense*) protect from inflammation and immune suppression induced by UV radiation." Photochemistry & Photobiology 74(3): 465-70.

Young, J. M., et al. (1984). "The mouse ear inflammatory response to topical arachidonic acid." Journal of Investigative Dermatology. 82(4): 367-71.

The invention claimed is:

1. A compound of the general formula (I):

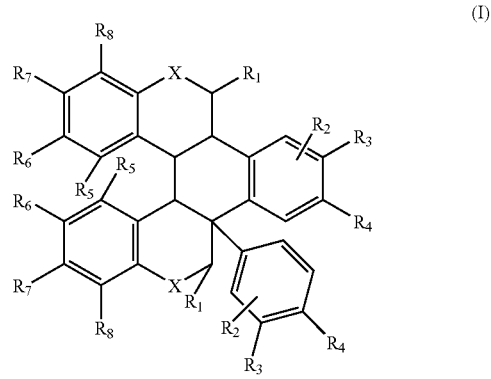

wherein
$R_1$, $R_2$, $R_3$, $R_4$, $R_5$, $R_6$, $R_7$ and $R_8$ are independently hydrogen, hydroxy, $OR_9$, $OC(O)H$, $OC(O)R_9$, $OSi(R_{10})_3$, $C(O)R_{11}$, $CO_2R_{12}$, alkyl, haloalkyl, cycloalkyl, aryl, arylalkyl, thiol, alkylthio, amino, alkylamino, dialkylamino, nitro, cyano or halo, $R_9$ is alkyl, haloalkyl, aryl, arylalkyl or alkylaryl, $R_{10}$ is independently hydrogen, alkyl or aryl, $R_{11}$ is hydrogen alkyl, aryl, arylalkyl or an amino acid, $R_{12}$ is hydrogen, alkyl, haloalkyl, aryl or arylalkyl, and X is O, which compounds may be optionally substituted or a pharmaceutically acceptable salt thereof.

2. The compound according to claim 1 of the general formula (Ia):

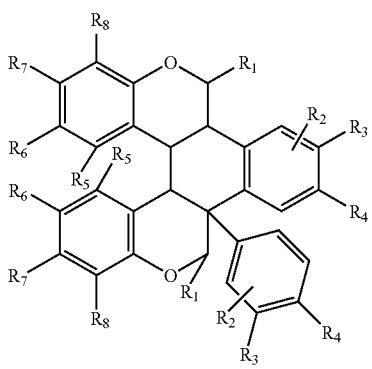

wherein $R_1$ is hydrogen or $C_{1-6}$-alkyl, $R_2$, $R_3$ and $R_4$ are independently hydrogen, hydroxy, $OR_9$, $OC(O)R_9$, $OSi(R_{10})_3$, $C_{1-6}$-alkyl, aryl, aryl-$C_{1-6}$-alkyl or halo, $R_5$, $R_6$, $R_7$ and $R_8$ are independently hydrogen, hydroxy, $OR_9$, $OC(O)R_9$, $OSi(R_{10})_3$, $C_{1-6}$-alkyl, aryl, aryl-$C_{1-6}$-alkyl or halo, $R_9$ is $C_{1-6}$-alkyl, fluoro-$C_{1-6}$-alkyl or aryl-$C_{1-6}$-alkyl, and $R_{10}$ is independently $C_{1-6}$-alkyl;

or a pharmaceutically acceptable salt thereof.

3. The compound according to claim 1 of the general formula (Ib):

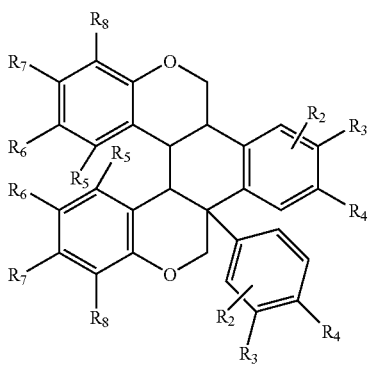

wherein $R_2$, $R_3$, $R_5$, and $R_8$ are independently hydrogen, hydroxy, $OR_9$, $OC(O)R_9$, $OSi(R_{10})_3$, methyl, ethyl, propyl, isopropyl, sec-butyl, t-butyl, phenyl or benzyl, $R_4$ and $R_7$ are independently hydrogen, hydroxy, $OR_9$, $OC(O)R_9$ or $OSi(R_{10})_3$, $R_6$ is hydrogen, hydroxy, $OR_9$, $OC(O)R_9$ or $OSi(R_{10})_3$, $R_9$ is methyl, ethyl, propyl, isopropyl, sec-butyl, t-butyl, phenyl or benzyl, and $R_{10}$ is independently methyl, ethyl or t-butyl, or a pharmaceutically acceptable salt thereof.

4. The compound according to claim 3, wherein $R_2$, $R_3$, $R_5$, and $R_8$ are independently hydrogen, hydroxy, $OR_9$, $OC(O)R_9$ or methyl, $R_4$ and $R_7$ are independently hydroxy, $OR_9$ or $OC(O)R_9$, $R_6$ is hydrogen $R_8$ is hydrogen, hydroxy, $OR_9$, $OC(O)R_9$ or methyl, and $R_9$ is methyl or benzyl, or a pharmaceutically acceptable salt thereof.

5. The compound according to claim 4, wherein $R_4$ is methoxy.

6. The compound according to claim 4, wherein $R_3$ and $R_4$ are methoxy.

7. The compound according to claim 4, wherein $R_8$ is methyl.

8. The compound according to claim 4 selected from:

4,9-Dihydroxy-14,15-dimethoxy-12a-(3',4'-dimethoxyphenyl)-2,11-dioxa-(1H,12H)-6b,6c,12a,16b-tetrahydronaphtho[1,2-g]chrysene (1)

4,9-Diacetoxy-14,15-dimethoxy-12a-(3,4'-dimethoxyphenyl)-2,11-dioxa-(1H,12H)-6b,6c,12a,16b-tetrahydronaphtho[1,2-g]chrysene (1-Ac)

4,9-Dihydroxy-14,15 -dimethoxy-12a-(3',4'-dimethoxyphenyl)-3,10-dimethyl-2,11-dioxa-(1H,12H)-6b,6c,12a,16b-tetrahydronaphtho[1,2-g]chrysene (2)

4,9-Diacetoxy-14,15-dimethoxy-12a-(3',4'-dimethoxyphenyl)-3,10-dimethyl-2,11-dioxa-(1H,12H)-6b,6c,12a,16b-tetrahydronaphtho[1,2-g]chrysene (2-Ac)

4,9-Dihydroxy-14-methoxy-12a-(4'-methoxyphenyl)-2,11-dioxa-(1H,12H)-6b,6c,12a,16b-tetrahydronaphtho[1,2-g]chrysene (3)

4,9-Diacetoxy-14-methoxy-12a-(4'-methoxyphenyl)-2,11-dioxa-(1H,12H)-6b,6c,12a,16b-tetrahydronaphtho[1,2-g]chrysene (3-Ac)

4,9-Dihydroxy-14-methoxy-12a-(4'-methoxyphenyl)-3,10-dimethyl-2,11-dioxa-(1H,12H)-6b,6c,12a,16b-tetrahydronaphtho[1,2-g]chrysene (4)

4,9-Diacetoxy-14-methoxy-12a-(4'-methoxyphenyl)-3,10-dimethyl-2,11-dioxa-(1H,12H)-6b,6c,12a,16b-tetrahydronaphtho[1,2-g]chrysene (4-Ac)

4,9,14-Trihydroxy-12a-(4'-hydroxyphenyl)-3,10-dimethyl-2,11-dioxa-(1H,12H)-6b,6c,12a,16b-tetrahydronaphtho[1,2-g]chrysene (5)

4,9,14-Triacetoxy-12a-(4'-acetoxyphenyl)-3,10-dimethyl-2,11-dioxa-(1H,12H)-6b,6c,12a,16b-tetrahydronaphtho[1,2-g]chrysene (5-Ac)

4,9-Dihydroxy-15-methoxy-12a-(3'-methoxyphenyl)-2,11-dioxa-(1H,12H)-6b,6c,12a,16b-tetrahydronaphtho[1,2-g]chrysene (6)

4,9-Diacetoxy-15-methoxy-12a-(3'-methoxyphenyl)-2,11-dioxa-(1H,12H)-6b,6c,12a,16b-tetrahydronaphtho[1,2-g]chrysene (6-Ac)

4,9,15-Trihydroxy-12a-(3'-hydroxyphenyl)-3,10-dimethyl-2,11-dioxa-(1H,12H)-6b,6c,12a,16b-tetrahydronaphtho[1,2-g]chrysene (7)

4,9,15-Triacetoxy-12a-(3'-acetoxyphenyl)-3,10-dimethyl-2,11-dioxa-(1H,12H)-6b,6c,12a,16b-tetrahydronaphtho[1,2-g]chrysene (7-Ac).

9. A method for the preparation of a compound of formula (I) according to claim 1 which method includes the step of reacting a compound of the formula (II):

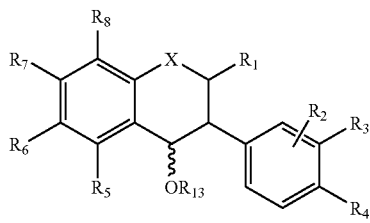 (II)

wherein $R_1, R_2, R_3, R_4, R_5, R_6, R_7$ and $R_8$ are independently hydrogen, hydroxy, $OR_9$, $OC(O)H$, $OC(O)R_9$, $OSi(R_{10})_3$, $C(O)R_{11}$, $CO_2R_{12}$, alkyl, haloalkyl, cycloalkyl, aryl, arylalkyl, thiol, alkylthio, amino, alkylamino, dialkylamino, nitro, cyano or halo, $R_9$ is alkyl, haloalkyl, aryl, arylalkyl or alkylaryl, $R_{10}$ is independently hydrogen, alkyl or aryl, $R_{11}$ is hydrogen alkyl, aryl, arylalkyl or an amino acid, $R_{12}$ is hydrogen, alkyl, haloalkyl, aryl or arylalkyl, $R_{13}$ is hydrogen, $R_9$, $C(O)R_9$, $Si(R_{10})_3$, alkylsulfonyl or benzenesulfonyl, and X is O, which compounds may be optionally substituted or a pharmaceutically acceptable salt thereof, with a coupling agent.

10. A method for the treatment, prophylaxis or amelioration of a disease which method includes the step of administering a therapeutically effective amount of one or more compounds of formula (I) as defined in claim 1 to a subject in need thereof, wherein the disease or disorder is selected from cancer, the unwanted proliferation or upregulation of cellular growth, inflammation or inflammatory disorders, autoimmune disorders, cardiovascular disorders and disorders associated with estrogen receptor activation.

11. The method of claim 10, wherein the treatment is the treatment of pain associated with inflammation.

12. The method of claim 10, wherein the inflammatory disorder is inflammatory bowel disease, ulcerative colitis, ulcerative proctitis, distal colitis or Crohn's disease.

13. The method of claim 10, wherein the treatment of the inflammatory disorder is absent cardiovascular side effects and/or is gut protective.

14. The method of claim 13, wherein the treatment is cardioprotective.

15. The method of claim 10, wherein the cancer is selected from leukaemia, glioma, melanoma, prostatic, ovarian, breast, colorectal, lung and pancreatic cancer.

16. A pharmaceutical composition which comprises one or more compounds of formula (I) as defined in claim 1 in association with one or more pharmaceutical carriers and/or excipients.

17. A method of increasing or restoring the sensitivity of cancer cells or a tumour to a chemotherapeutic agent by contacting said cells or tumour with an isoflavonoid dimer of formula (I) as defined in claim 1.

18. The method according to claim 17, wherein the chemotherapeutic agent is a growth receptor inhibitor or death receptor stimulator.

* * * * *